US009204642B2

(12) United States Patent
Koschnick et al.

(10) Patent No.: US 9,204,642 B2
(45) Date of Patent: Dec. 8, 2015

(54) HERBICIDAL COMPOSITIONS AND METHODS

(71) Applicant: SePRO Corporation, Carmel, IN (US)

(72) Inventors: Tyler J. Koschnick, Westfield, IN (US); Jessica Koczan, Whitakers, NC (US)

(73) Assignee: SePro Corporation, Carmel, IN (US)

( * ) Notice: Subject to any disclaimer, the term of this patent is extended or adjusted under 35 U.S.C. 154(b) by 0 days.

(21) Appl. No.: 14/332,036

(22) Filed: Jul. 15, 2014

(65) Prior Publication Data

US 2014/0352213 A1 Dec. 4, 2014

Related U.S. Application Data

(63) Continuation of application No. PCT/US2014/034526, filed on Apr. 17, 2014.

(60) Provisional application No. 61/813,166, filed on Apr. 17, 2013, provisional application No. 61/814,600, filed on Apr. 22, 2013.

(51) Int. Cl.
*A01N 43/40* (2006.01)
*A01N 43/84* (2006.01)
*A01N 41/04* (2006.01)
*A01C 21/00* (2006.01)

(52) U.S. Cl.
CPC ............... *A01N 43/40* (2013.01); *A01C 21/00* (2013.01); *A01N 41/04* (2013.01); *A01N 43/84* (2013.01)

(58) Field of Classification Search
CPC ....... A01N 43/40; A01N 43/84; A01N 41/04; A01C 21/00
See application file for complete search history.

(56) References Cited

U.S. PATENT DOCUMENTS

| | | | |
|---|---|---|---|
| 5,596,124 | A | 1/1997 | Cary et al. |
| 6,713,433 | B2 | 3/2004 | Jimoh |
| 7,060,657 | B2 | 6/2006 | Hacker et al. |
| 8,129,564 | B2 | 3/2012 | Prosch et al. |
| 8,338,332 | B1 | 12/2012 | Hacker et al. |
| 2003/0130120 | A1 | 7/2003 | Ziemer et al. |
| 2006/0276341 | A1 | 12/2006 | Zagar et al. |
| 2007/0021303 | A1 | 1/2007 | Rosinger et al. |
| 2008/0153704 | A1 | 6/2008 | Yamaji et al. |
| 2008/0312081 | A1 | 12/2008 | LeBlanc et al. |
| 2010/0130363 | A1 | 5/2010 | Satchivi et al. |
| 2011/0190136 | A1 | 8/2011 | Hufnagl et al. |

FOREIGN PATENT DOCUMENTS

| | | | |
|---|---|---|---|
| EP | 23100 | A1 * | 1/1981 |
| EP | 1128729 | B1 | 5/2003 |
| EP | 1215962 | B1 | 2/2005 |

OTHER PUBLICATIONS

Brake F2, Product Label, [online], SePRO, 2013 [retrieved on Apr. 1, 2015]. Retrieved from the Internet:<URL:http://www.kellysolutions.com/erenewals/documentsubmit/KellyData%5CSC%5Cpesticide%5CProduct%20Label%5C67690%5C67690-EXEMPT%5C67690-EXEMPT_BRAKE_F2_4_18_2013_9_12_06_AM.pdf>, pp. 1-15.*
Whitaker, J.R,. Palmer Amaranth (Amaranthus palmeri) Control in Soybeans with Glyphosate and Conventional Herbicide Systems, 2010, Weed Technology, vol. 24, Issue 4, pp. 403-410.*
Poston, D.H., Texasweed (Caperonia palustris) Control in Soybean with Postemergence Herbicides, 2007, Weed Technology, vol. 21, pp. 670-673.*
International Search Report and Written Opinion issued in PCT/US2014/034526, Aug. 1, 2014.
Albritton, R.; Parka, S. J., 1978: Studies Evaluating the Site of Fluridone Uptake by Fourteen Crop and Ten Weed Species, 253-259.
D.F. Berard, D.P. Rainey, C.C. Lin, Absorption, Translocation, and Metabolism of Fluridone in Selected Crop Species, Weed Science Scoeity of America, Weed Science, vol. 26, No. 3 May 1978, pp. 252-254.
Najib Malik and Donald S.H. Drennan, Journal of Environmental Science and Health, Part B: Pesticides, Food Contaminants, and Agricultural Wastes, Bioavailability and dissipation of fluridone under controlled conditions, Published online: Nov. 21, 2008.
P.A. Banks and M.G. Merkle, Field Evaluations of the Herbicidal Effects of Fluridone on Two Soils, Agronomy Journal, vol. 71, Sep.-Oct. 1979.
P.A. Banks and M.G. Merkle, Weed Science Society of America, Soil Detection and Mobility of Fluridone, Weed Science, vol. 27, No. 3, May 1979, pp. 309-312.
S.J. Parka, R. Albritton, C. Lin, Correlation of Chemical and Physical Properties of the Soil With Herbicidal Activity of Fluridone, 1978.
Sheldon D. West and Stanley J. Parks, Residues in Crops and Soils Irrigated with Water Containing the Aquatic Herbicide Fluridone, J. Agric Food Chem. 1992, vol. 40, pp. 160-164.
Banks et al., Soil Detection and Mobility of Fluridone, Weed Science, vol. 27, No. 3 (May 1979) pp. 309-312.
Banks et al., The Persistence of Fluridone in Various Soils under Field and Controlled Conditions, Weed Science, vol. 27, No. 6 (Nov. 1979) pp. 631-633.
Berard et al., Absorption, Translocation, and Metabolism of Fluridone in Selected Crop Species, Weed Science, vol. 26, No. 3 (May 1978), pp. 252-254.
Brake F2 Herbicide, http://www.sepro.com/brake/About-Brake-F2.aspx.
International Survey of Herbicide Resistant Weeds, Accessed Apr. 4, 2013.

(Continued)

*Primary Examiner* — Sue Liu
*Assistant Examiner* — Andriae M Holt
(74) *Attorney, Agent, or Firm* — Woodard, Emhardt, Moriarty, McNett & Henry LLP

(57) ABSTRACT

Described are preferred methods and compositions for controlling weeds in soil that involve the use of a bleaching herbicide such as fluridone in combination with at least one other additional selected herbicidal agent, which is preferably a PPO-inhibitor such as fomesafen or flumioxazin. Also described are safening effects of bleaching herbicidal agents such as fluridone on other herbicides, and of other herbicides on bleaching herbicidal agents.

30 Claims, 29 Drawing Sheets

(56) References Cited

OTHER PUBLICATIONS

Joanna Davies, Herbicide Safeners—Commerical Products and Tools for Agrochemical Research, Pesticide Outlook, The Royal Society of Chemistry, Feb. 2001, pp. 10-15.

Keeley et al., Comparison of Six Cropping Systems for Yellow Nutsedge (Cyperus esculentus) Control, Weed Science, vol. 31, No. 1 (Jan. 1983) pp. 63-67.

Lars W. J. Anderson, Effect of Light on the Phytotoxicity of Fluridone in American Pondweed (Potamogeton nodosus) and Sago Pondweed (P. pectinatus), Weed Science, vol. 29, No. 6 (Nov. 1981) pp. 723-728.

Main et al., Weed Science, Cotton Tolerance to Fomesafen Applied Preemergence, vol. 16, pp. 80-87, 2012.

Rafii et al., Influence of Site of Uptake of Fluridone on Early Development of Soybean (Glycine max) and Cotton (Gossypium hirsutum), Weed Science, vol. 27, No. 3 (May 1979), pp. 321-327.

Rafil et al., Metabolic Sites of Action of Fluridone in Isolated Mesophyll Cells, Weed Science, vol. 27, No.4 (Jul. 1979), pp. 422-426.

Schroeder et al., Persistence of Fluridone in Five Georgia Soils, Weed Science, vol. 34, No. 4 (Jul. 1986), pp. 612-616.

Sharp et al., Persistence of Cotton (Gossypium hirsutum) Herbicides and Injury to Replacement Soybeans (Glycine max) after Stand Failure, Weed Science, vol. 30, No. 1 (Jan. 1982) pp. 109-115.

Shea et al., Effect of Soil pH on Fluridone Activity and Persistence as Determined by Chlorophyll Measurements, Weed Science, vol. 31, No. 3 (May 1983) pp. 347-350.

Valent, Valor SX Herbicide Labels, for Control and/or Suppression of Certain Weeds in Cotton, Dry Beans, Field Corn, Peanut, Soybean, Sugarcane, Sweet Potato, Fallow Land and to Maintain Bare Ground on Non-Crop Areas of Farms, 2010.

* cited by examiner

A          B

A

B 6.1.    6.2.    6.3.    6.4.    6.5.

12.1.  12.2.  12.3.

18.1. 18.2. 18.3.

23.1. 23.2. 23.3.

HERBICIDAL COMPOSITIONS AND METHODS

REFERENCE TO RELATED APPLICATIONS

This application is a continuation of and claims the benefit of priority to International Application No. PCT/US2014/034526, filed Apr. 17, 2014, which claims the benefit of U.S. Provisional Patent Application No. 61/813,166, filed Apr. 17, 2013, and U.S. Provisional Patent Application No. 61/814,600, filed Apr. 22, 2013, each of which is hereby incorporated by reference in its entirety.

FIELD OF THE INVENTION

The present invention relates generally to herbicidal compositions and methods.

BACKGROUND

Herbicides have been widely used to kill unwanted plants or weeds in crop fields. Glyphosate, also called Roundup®, is a common agricultural herbicide. This herbicide class functions by blocking the shikimate pathway in plants. The use of glyphosate resistant crop strains, also known as Roundup Ready® crops, in conjunction with glyphosate herbicide has increased crop yields and reduced costs for farmers. The use of glyphosate dramatically decreased the reliance on preemergent or residual herbicides as most production agriculture transformed to using postemergent applied glyphosate only. However, the emergence of glyphosate resistant weeds presents a growing problem for farmers. Weeds not killed by glyphosate necessitate the use of additional or larger quantities of herbicides, as well as a decrease in use of no-till farming methods, both of which increase the cost of farming.

Another class of herbicides is called Protoporphyrinogen oxidase (PPO) inhibitors. Herbicides in this class block the oxidation of the protoporphyrinogen within the chloroplast of a plant cell. Oxidation of protoporphyrinogen is critical for the production of protoporphyrin IX, a precursor molecule necessary for the metabolic synthesis of chlorophyll (a component of photosynthesis) and heme (an element of electron chain transport). Examples of PPO inhibitors include acifluorfen, carfentrazone, flumioxazin, flumiclorac, fluthiacet, fomesafen, lactofen, oxyfluorfen, pyraflufen-ethyl, saflufenacil and sulfentrazone. In practice, PPO-inhibitors are generally not used as postemergent herbicides across a wide-range of crops due to the potential for injury or killing the crops. They have limited uses as a foliar spray, primarily as a defoliant or desiccant. PPO-inhibitors are primarily applied preplant, or used weeks before crops are planted, to avoid potential phytotoxicty on emerging crop seeds from the residual remaining in the soil. This interval between application and planting allows residues to degrade for greater crop safety. However, preplant applications also reduce the longevity of weed control after the crops are planted because the herbicide starts to lose activity as crops are planted. This necessitates the need for additional weed control measures after planting. Some PPO-inhibitors contain use directions that require rainfall following the application and before crops are planted to mitigate potential crop phytotoxicity. Thus, the use of PPO-inhibitors as preemergence herbicide just before, at, or immediately after planting is relatively limited, or very crop specific, due to significant concern over crop injury. Resistance to PPO inhibitors has been documented, but not at the magnitude of glyphosate resistance, causing farmers and industry alike to caution the repeated application of PPOs as a single chemistry herbicide.

Fluridone, 1-methyl-3-phenyl-5-[3-(trifluoromethyl)phenyl]-4(1H)-pyridone, is a herbicide in the class of bleaching herbicides. Fluridone's mode of action inhibits the biosynthesis of carotenoid precursors. Carotenoid pigments protect chlorophyll from photodegredation. The inhibition of the synthesis of the precursors allows for the chlorophyll to become susceptible to degradation. Fluridone is commonly used in aquatic applications, and has also been used in agricultural settings, such as for controlling weeds in fields. Fluridone is sold under several trade names, including Brake™ (SePRO Corporation, Carmel, Ind.). Fluridone is a relatively broad spectrum herbicide that cannot be used in many crops due to the potential for phytotoxicity. However, cotton is one crop that is quite tolerant to fluridone.

In view of this background, need remains in the area of improved herbicidal methods and compositions useful for controlling weeds, particularly in an agricultural context.

SUMMARY

In one aspect, the present invention provides for improved methods and compositions for controlling weeds, for example in an agricultural setting. Such weeds can be, for example, but is not limited to, *Amaranthus palmeri* (optionally glyphosate resistant), also called *Palmer amaranth*, Palmer pigweed or *P. amaranth*, in cotton or other field crops. Other agricultural crops suitable for methods of the current invention include sweet potatoes, broccoli, peanuts, melons, soybeans, sunflower, dry beans, rice, corn, fruit, nuts, grapes, tree, or vine crops. These or other crops can be generated from any suitable plant-generating material including for example seeds, tubers, slips, seed plants, roots or other plant parts, and the like.

In another aspect, the present invention provides herbicidal methods and compositions that include a bleaching herbicide, or phytoene desaturase inhibiting herbicide (PDS-inhibitor), such as fluridone, norflurazon or another phytoene desaturase inhibiting herbicide (PDS-inhibitor), and a second herbicide, such as a PPO-inhibitor herbicide. Preferably, the PPO-inhibitor or other second herbicide does not require water, or requires lower amounts of water than the first herbicide (e.g. bleaching herbicide), for activation. Herbicides used in embodiments of the present invention may be used as salts and/or esters in addition to use in their free acid or free base form.

In additional aspects, fluridone has unexpectedly been found to safen or reduce the damage caused to a plant by a second herbicide, in particular where the plant exhibits a significant phytotoxic response to the second herbicide. As well, other herbicides have been found to safen or reduce the damage caused to a plant by fluridone, in particular where the plant exhibits a significant phytotoxic response to fluridone. Safeners generally reduce the effect of the herbicide on crop plants and/or improve the selectivity between crop plants as compared to the weed or weeds being targeted by the herbicide. Suitable second herbicides of the present invention for use with fluridone, or with other similar bleaching herbicides, include but are not limited to acetochlor, acifluorfen, carfentrazone, dicamba, diuron, flumiclorac, fluthiacet, fluometuron, flumioxazin, fomesafen, lactofen, metolachlor, oxyfluorfen, pendimethalin, pyraflufen-ethyl, pyrithiobac-sodium, pyroxasulfone, saflufenacil or sulfentrazone. In certain preferred embodiments, the second herbicide that is safened by fluridone, or another bleaching herbicide, is fomesafen or flumioxazin, especially in cotton plants. In additional preferred embodiments, the second herbicide that safens fluridone, or another bleaching herbicide, is flumioxazin or fomesafen, especially in soybean plants. Fluridone may also safen other herbicides used, and when two herbicides are used in combination, they may safen each other.

Additional embodiments of the invention, as well as features and advantages thereof, will be apparent from the descriptions herein.

DETAILED DESCRIPTION

Figure 1:
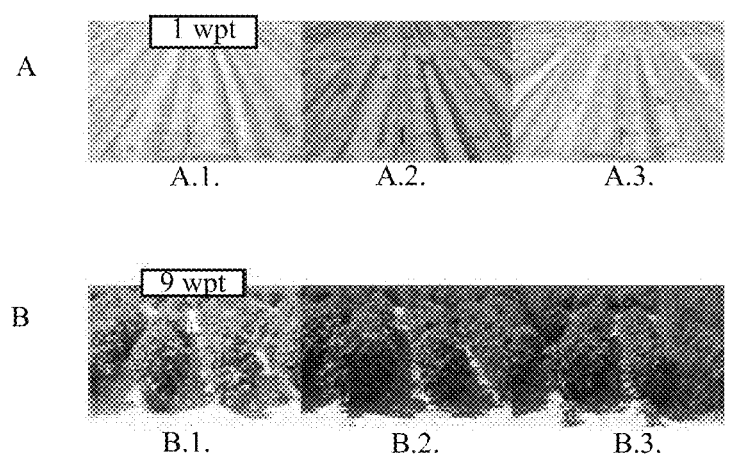
FIG. 1 shows digital images of field treatments at various active ingredient (ai) application rates. No difference was seen between treatments due to ideal growing and optimal herbicide efficacy conditions. No phytotoxicity was seen at any treatment. All exhibited great control compared to the untreated control. Top pictures were taken one week post treatment (wpt) and bottom image was taken at 9 wpt. Digital image A.1. shows a field 1 wpt where Brake was applied at the rate of 0.2 lb ai/A. Digital image A.2. shows a field 1 wpt where BrakeF2 was applied (0.2:0.125 lb/ai/A). Digital image A.3. shows a field 1 wpt where Fomesafen was applied at the rate of 0.2 lb ai/A. Digital image B.1. shows a field 9 wpt where Brake was applied at the rate of 0.2 lb ai/A. Digital image B.2. shows a field 9 wpt where BrakeF2 was applied (0.2:0.125 lb/ai/A). Digital image B.3. shows a field 9 wpt where Fomesafen was applied at the rate of 0.2 ai/A.

For the purposes of promoting an understanding of the principles of the invention, reference will now be made to certain embodiments and specific language will be used to describe the same. It will nevertheless be understood that no limitation of the scope of the invention is thereby intended, such alterations and further modifications, and such further applications of the principles of the invention as described herein being contemplated as would normally occur to one skilled in the art to which the invention relates.

As discussed above, aspects of the present invention relate to methods and compositions involving the use of a bleaching herbicide, such as fluridone, diflufenican, picolinafen, beflubatamid, fluorochloridone, flurtamone, fluometuron, and/or norflurazon, in combination with certain other herbicidal agents, especially PPO-inhibitors, for controlling weeds including but not limited to glyphosate resistant weeds in an agricultural setting. The two herbicides in combination can provide enhanced control of weeds and/or improved safety to the crop when applied for example before the emergence of plants from seeds or another plant-generating material, for instance applied in pre-planting or pre-emergent fashion. This enhanced control can for example be achieved under initial dry conditions after planting when little or no water is added to the soil (e.g., in the form of rainfall or by irrigation).

As used in this specification, and unless otherwise indicated, the term "herbicide" refers to a molecule or combination of molecules that retards or otherwise kills undesirable, unwanted plants such as, but not limited to, deleterious or annoying weeds, broadleaf plants, grasses, and sedges; and may be used in this manner for crop protection. "Herbicide" also refers to any salt and/or ester forms of a herbicide as well as the free acid or free base form of the herbicide. The phrase "effective amount" means an amount of herbicide necessary to produce an observable desired effect to reduce unwanted plant growth, including the effects of plant necrosis, plant death, growth inhibition, reproduction inhibition, inhibition of proliferation, and removal, destruction, or otherwise diminishing the occurrence and activity of undesirable, unwanted plants. Undesirable, unwanted plants include herbicide-tolerant or herbicide-resistant weeds such as glyphosate-tolerant weeds. The term "chlorosis" means a condition where plant leaves produce insufficient chlorophyll.

There are many ways to measure and/or assess damage to a plant, for example the number or percentage of all leaves with visible bleaching injury may be measured and/or calculated (PHYBLE) as a measure of chlorosis. In addition, or alternatively, the number or percentage of cotyledons with excessive wrinkling and/or brown spotting due to herbicidal injury (PHYGEN) may be measured and/or calculated as a measure of injury to the plant.

Cotton (*Gossypium* spp.) is the world's most important textile fiber crop and is one of the world's most important oilseed crops. Cotton plants provide a source of human food, livestock feed, and raw material for industry. Cottonseed is pressed for cooking oil and the residual cottonseed meal is used for animal feed. Industrial uses of cotton include candlewicks, twine, paper and a multitude of fabric products. The genus *Gossypium* is very large, containing about 50 species. Two tetraploid species of *Gossypium* have spinnable seed fibers called lint. These two species are *G. hirsutum* (referred to as American Upland cotton) and *G. barbadense* (referred to as Pima cotton).

Cotton is a dichotomous plant with perfect flowers, i.e., cotton has male, pollen-producing organs and separate female, pollen-receiving organs on the same flower. The cultivated cotton flower is surrounded by three triangular bracts forming what is commonly known as squares. The flower contains an open corolla with five petals, a staminal column bearing clusters of stamens and forming a tube that encloses the style. The compound pistil consists of three to five carpels with stigmas protruding above the anthers. The ovary develops into a three- to five-loculed capsule or boll. From seven to nine seeds are set within each lock or locule. On the day preceding anthesis, a twisted corolla emerges from the square. On the day of anthesis, the corolla opens and pollen shedding occurs. The corolla turns red the day following anthesis and later falls from the plant. Pollination occurs with the opening of the anthers and shedding of pollen on the stigma or with the deposit of pollen on the stigma by insects.

Cotton is slow growing by nature, often times more similar to trees than other important agronomic crops. It requires hot weather to grow, delaying the majority of its growth until later in the season. The majority of weeds, or unwanted plant material, are not restricted by these weather constraints. This puts cotton at a disadvantage over a large number of weeds, which are fast growing and can often out compete cotton early in the season. Thus it is essential that herbicides are included in any cotton program. Unfortunately, due to a number of reasons, mostly economical, there are a limited number of herbicides that are used in weed control for cotton, and a number of weeds have developed resistance to some chemistries that are available to cotton growers, in particular, glyphosate.

One of the most impactful glyphosate-resistant weeds that farmers face is *P. amaranth*. A survey taken by Southwest Press states that over 50% of American Upland cotton contains resistant *P. amaranth*. In response to this epidemic, farmers have increased usage of other chemistries, which has led to nearly a doubling of the cost of chemical input per acre. A number of growers have resorted to wicking, or hand hoeing the plants out, at a much more significant cost of chemical and labor.

Herbicides describe below may be used in embodiments of the present invention in their free acid or free base form as well as the salt, for example sodium salt, and/or ester derivatives.

In certain embodiments of the present invention, fluridone can be applied to soil at a rate of up to about 0.5 pounds per acre and/or 0.4 pounds per acre, for example in the range of about 0.05 pounds per acre to about 0.5 pounds per acre and/or about 0.05 pounds per acre to about 0.4 pounds per acre. In other embodiments, fluridone can be applied to soil at a rate of about 0.1 pounds per acre to about 0.4 pounds per acre. In another embodiment, fluridone can be applied to soil at a rate of about 0.2 pounds per acre to about 0.4 pounds per acre. In still another embodiment, fluridone can be applied to soil at a rate of about 0.3 pounds per acre to about 0.4 pounds per acre.

In certain work to date, fomesafen was evaluated for use with fluridone either in a combination application or as sequentially applied. A product including a mixture of fluridone and fomesafen was designated as the Brake F2™ product. Fomesafen is a member of the PPO inhibitor herbicide class and may be applied pre-plant, pre-emergence or post-emergence (which can be conducted through post-directed spraying to avoid contact with the plant leaves) commonly for control or suppression of broadleaf weeds, grasses and sedges. Fomesafen has the chemical name 5-[2-chloro-4-(trifluoromethyl)phenoxy]-N-(methylsulfonyl)-2-nitrobenzamide and may also be used as the sodium salt thereof. In one embodiment, fomesafen may be applied in concert with fluridone at a ratio in the range of about 0.1:1 w/w (fluridone:fomesafen) and/or about 0.5:1 to about 10:1 w/w (fluridone:fomesafen), or about 0.75:1 w/w (fluridone:fomesafen) to about 10:1 w/w (fluridone:fomesafen). In another embodiment, fomesafen may be applied in concert with fluridone at a ratio in the range of about 0.75:1 w/w (fluridone:fomesafen) to about 8:1 w/w (fluridone:fomesafen). In still another embodiment, fomesafen may be applied in concert with fluridone at a ratio in the range of about 0.75:1 w/w (fluridone:fomesafen) to about 5:1 w/w (fluridone:fomesafen). In more preferred embodiments, fomesafen may be applied in concert with fluridone at a ratio in the range of about 0.75:1 w/w (fluridone:fomesafen) to about 4:1 w/w (fluridone:fomesafen). In these applications, embodiments include those in which the fluridone is applied at any of the rates (pounds per acre) specified herein. In still another embodiment, fluridone can be used in as low of a ratio as about 0.1:0.1 w/w (fluridone:fomesafen).

The combination of herbicides can provide enhanced control of weeds, including for example, *Palmer amaranth*, as compared to a corresponding treatment using fluridone alone. This enhanced control as compared to fluridone alone can be observed particularly under conditions in which the soil receives little or no water (e.g. in the form of rainfall) in the period immediately following (e.g. two weeks following) application of the combination. Fluridone requires more moisture for activation than some of the other soil applied herbicides for activation, and thus under such relatively dry initial conditions the fomesafen can help to prevent weed breakthrough. This same effect can be provided in other selected combinations of fluridone or another bleaching herbicide such as norflurazon with fomesafen or other PPO herbicides.

Figure 3A:
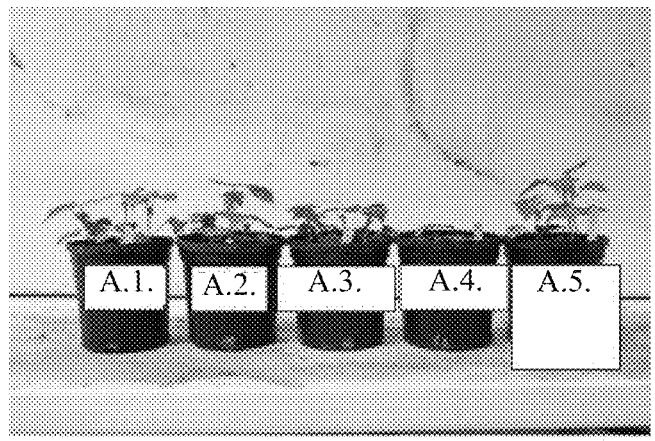
FIG. 3 shows digital images from a greenhouse trial. UTC is "untreated control." Brake is fluridone. BrakeF2 is fluridone plus fomesafen. Growth of treated cotton plants 4 weeks after planting (FIG. 3a) is shown. Fomesafen has a stunting effect on cotton. Brake F2 is able to safen fomesafen. Digital image A shows a series of cotton plants 4 weeks after planting. A.1. is untreated control (UTC). A.2. is Brake 0.2 lb ai/A. A.3. is Fomesafen 0.125 lb ai/A. A.4. is fomesafen 0.2 lb ai/A. A.5. is Brake F2: Brake 0.2 lb ai/A with Fomesafen 0.125 lb ai/A. Digital images B show a series of cotton plants 4 weeks after planting. B.1. and B.2. are untreated controls. B.3. and B.4. are Brake 0.2 lb ai/A. B.5. and B.6. are Fomesafen 0.2 lb ai/A. B.7. and B.8. are BrakeF2.
Figure 3B:
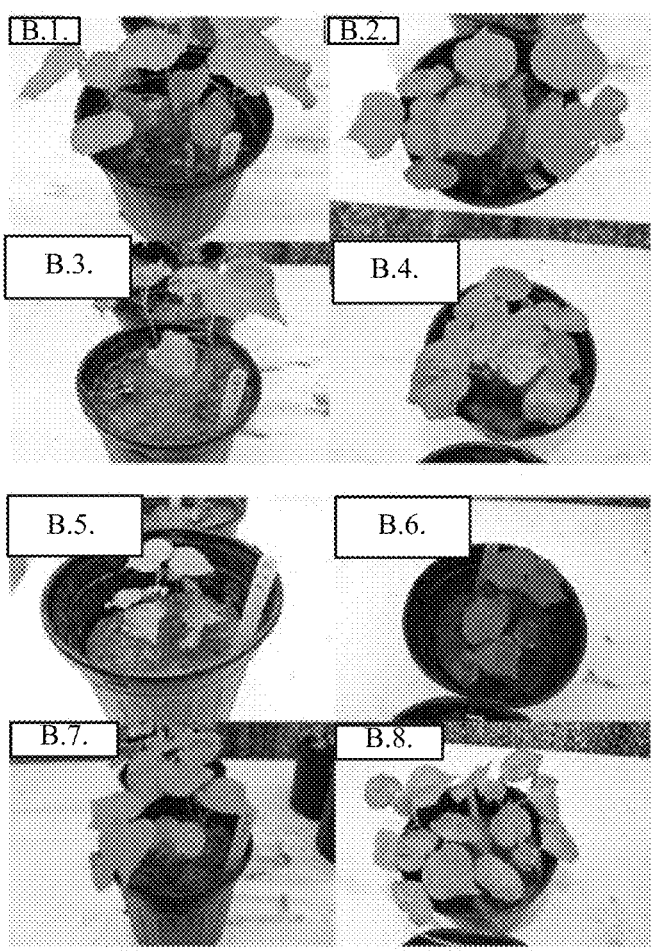

Unexpectedly also, it has been observed that fluridone has a safening affect on fomesafen, flumioxazin and/or other herbicides. Herbicides may alternatively may have a safening effect on fluridone, or two herbicides may safen each other in certain applications. This affect was measured by observing the size and height of plants as well as lack of stunting to the cotyledon, and lack of spots or other phytotoxic symptoms (such as chlorosis, necrosis, and other visual injury) on the leaves of plants. This affect can be observed in FIGS. 3a and 3b. In FIG. 3a, the pot on the far right shows a cotton plant treated with both fluridone and fomesafen. The pots to the left show cotton plants that were not treated with any herbicide as a control as well as plants treated with fluridone only and fomesafen only. The cotton plant treated with both fluridone and fomesafen is larger than the pots to the left by visual inspection.

Other PPO inhibitor herbicides can be used instead of or in addition to the fomesafen, in additional embodiments.

Figure 4:
FIG. 4 shows digital images of a demonstration of the safening effect of fluridone on herbicides. The pot on the left was treated with a herbicidal mixture of fluridone and flumioxazin. The pot on the right was treated with flumioxazin only and shows damage to cotton plant.

Flumioxazin is another herbicide member of the PPO-inhibitor class that is commonly applied pre-emergent to control weeds, and has the chemical name 2-[7-fluoro-3,4-dihydro-3-oxo-4-(2-propynyl)-2H-1,4-benzoxazin-6-yl]-4,5,6,7-tetrahydro-1H-isoindole-1,3(2H)-dione. In certain embodiments of the present invention, flumioxazin can be applied to soil at a rate of about 0.015 pounds per acre to about 0.25 pounds per acre. In other embodiments, flumioxazin can be applied to soil at a rate of about 0.03 pounds per acre to about 0.25 pounds per acre. In another embodiment, flumioxazin can be applied to soil at a rate of about 0.3 pounds per acre to about 0.2 pounds per acre. In applicants work, fluridone has exhibited a safening affect on flumioxazin in cotton. In certain embodiments, flumioxazin may be applied in concert with fluridone at a ratio in the range from about 15:1 w/w fluridone:flumioxazin to about 1:5 w/w fluridone:flumioxazin. FIG. 4 shows this safening effect. The pot on the left of FIG. 4 shows three cotton plants treated with both fluridone and flumioxazin. The pot to the right of FIG. 4 shows cotton plants treated only with flumioxazin, and although three cotton plants were planted, only one emerged from the soil and did so with significant damage to the plant as seen by the brown spots on the leaves.

Acifluorfen is a member of the PPO inhibitor herbicide class, and has the chemical name, 5-[2-Chloro-4-(trifluoromethyl)phenoxy]-2-nitrobenzoic acid. Acifluorfen is effective against broadleaf weeds and grasses and is used agriculturally on fields growing soybeans, peanuts, peas, and rice. In certain embodiments, acifluorfen is applied in concert with fluridone as disclosed herein.

Carfentrazone is a selective broadleaf herbicide member of PPO inhibitor herbicide family with a triazolinone moiety, and has the chemical name (RS)-2-chloro-3-{2-chloro-5-[4-(difluoromethyl)-4,5-dihydro-3-methyl-5-oxo-1H-1,2,4-triazol-1-yl]-4-fluorophenyl}propionic acid. In certain embodiments, carfentrazone is applied in concert with fluridone or another bleaching herbicide as disclosed herein.

Flumiclorac is a selective herbicide of the PPO inhibitor class for post emergence control and suppression of susceptible broadleaf weeds commonly used in corn and soybean fields, and has the chemical name [2-chloro-4-fluoro-5-(1,3,4,5,6,7-hexahydro-1,3-dioxo-2H-isoindol-2-yl)phenoxy] acetic acid. In certain embodiments, flumiclorac is applied in concert with fluridone or another bleaching herbicide as disclosed herein.

Fluthiacet or fluthiacet-methyl is a member of the PPO inhibitor class, and is commonly applied to actively growing weeds in soybeans to control annual broadleaf weeds, is particularly effective in controlling velvetleaf, and has the chemical name acetic acid[[2-chloro-4-fluoro-5-[(tetrahydro-3-oxo-1H,3H-[1,3,4]thiadiazolo[3,4-a]pyridazin-1-ylidene)amino]phenyl]thio]-methyl ester. In certain embodiments, fluthiacet is applied in concert with fluridone or another bleaching herbicide as disclosed herein.

Lactofen is a member of the PPO inhibitor herbicide class and is generally applied post-emergence, and has the chemical name ethyl O-[5-(2-chloro-α,α,α-trifluoro-p-tolyloxy)-2-nitrobenzoyl]-DL-lactate. In certain embodiments, lactofen is applied in concert with fluridone or another bleaching herbicide as disclosed herein.

Oxyfluorfen is a diphenyl-ether member of the PPO inhibitor herbicide class used for broad spectrum pre- and post-emergent control of annual broadleaf and grassy weeds in a variety of tree fruit, nut, vine, and field crops. Oxyfluorfen has the chemical name 2-chloro-α,α,α-trifluoro-p-tolyl 3-ethoxy-4-nitrophenyl ether. In certain embodiments, oxyfluorfen is applied in concert with fluridone or another bleaching herbicide as disclosed herein.

Sulfentrazone is a member of the PPO inhibitor herbicide class, and has the chemical name 2',4'-dichloro-5'-(4-difluoromethyl-4,5-dihydro-3-methyl-5-oxo-1H-1,2,4-triazol-1-yl)methanesulfonanilide. Sulfentrazone is primarily taken up by the roots of treated plants. Plants emerging from treated soil turn necrotic and die after exposure to light. Foliar contact causes rapid desiccation and necrosis of exposed plant tissue. Shoot-root soil placement studies indicate that sulfentrazone is primarily absorbed by the roots of the plant following soil applications. In certain embodiments, sulfentrazone is applied in concert with fluridone or another bleaching herbicide as disclosed herein.

Pyraflufen-ethyl is a member of the PPO inhibitor herbicide class that inhibits protoporphyrinogen IX oxidase that is normally applied post emergence to broad leaved weeds, and has the chemical name ethyl [2-chloro-5-(4-chloro-5-difluoromethoxy-1-methylpyrazol-3-yl)-4-fluorophenoxy]acetate. In certain embodiments, pyraflufen-ethyl is applied in concert with fluridone or another bleaching herbicide as disclosed herein.

Pyroxasulfone is a residual herbicide and is considered to be a seedling shoot growth inhibitor, and has the chemical name 3-[5-(difluoromethoxy)-1-methyl-3-(trifluoromethyl)pyrazol-4-ylmethylsulfonyl]-4,5-dihydro-5,5-dimethyl-1,2-oxazole. In certain embodiments, pyroxasulfone is applied in concert with fluridone or another bleaching herbicide as disclosed herein.

Saflufenacil is another residual herbicide. In certain embodiments, saflufenacil is aplied in concert with fluridone or another bleaching herbicide as disclosed herein. Saflufenacil can be applied sufficiently in advance of planting to avoid or essentially avoid crop injury, for example in certain aspects at least about 42 days in advance of planting.

Acetochlor is a member of the chloroacetanilide herbicide family, and has the chemical name 2-Chloro-N-(ethoxymethyl)-N-(2-ethyl-6-methylphenyl)acetamide. Acetochlor is commonly applied preemergence or as a preplant incorporated herbicide. In certain embodiments, acetochlor is applied in concert with fluridone or another bleaching herbicide as disclosed herein.

Dicamba is a selective herbicide in the chlorophenoxy family of chemicals, and has the chemical name 3,6-dichloro-2-methoxybenzoic acid. Dicamba is a growth hormone or auxin. These hormones help to control plant growth. When plants are treated with dicamba, they grow in abnormal and uncontrollable ways, and often, the plants die. Dicamba is commonly used on many broadleaf weeds and woody plants. In certain embodiments, dicamba is applied in concert with fluridone or another bleaching herbicide as disclosed herein.

Diuron, also called DCMU, has the chemical name 3-(3,4-dichlorophenyl)-1,1-dimethylurea. Diuron is a very specific and sensitive inhibitor of photosynthesis. It blocks the plastoquinone binding site of photosystem II, disallowing the electron flow from where it is generated, in photosystem II, to plastoquinone. In certain embodiments, diuron is applied in concert with fluridone or another bleaching herbicide as disclosed herein.

Fluometuron is a bleaching herbicide that is believed to inhibit photosynthesis and of carotenoid biosynthesis. Fluometuron has the chemical name 1,1-dimethyl-3-($\alpha,\alpha,\alpha$-trifluoro-m-tolyl)urea. Commonly fluometuron is used as a herbicide in cotton and sugarcane fields as a preplant, pre-emergence, and post-emergence herbicide for the control of broadleaf weeds and annual grasses. In certain embodiments, fluometuron is applied in concert with fluridone or another bleaching herbicide as disclosed herein.

Metolachlor is a member of the shoot growth inhibitor herbicide class, and has the chemical name 2-chloro-N-(6-ethyl-o-tolyl)-N-[(1RS)-2-methoxy-1-methylethyl]acetamide. In certain embodiments, metolachlor is applied in concert with fluridone or another bleaching herbicide as disclosed herein.

Pendimethalin is an herbicide used in premergence and postemergence applications to control annual grasses and certain broadleaf weeds. It inhibits cell division and cell elongation, and has the chemical name N-(1-ethylpropyl)-2,6-dinitro-3,4-xylidine. In certain embodiments, pendimethalin is applied in concert with fluridone or another bleaching herbicide as disclosed herein.

Pyrithiobac and the sodium salt thereof is a member of the ALS inhibitor herbicide class, and has the chemical name 2-chloro-6-(4,6-dimethoxypyrimidin-2-ylthio)benzoic acid. In certain embodiments, pyrithiobac or its sodium salt is applied in concert with fluridone or another bleaching herbicide as disclosed herein.

Other PPO-inhibitors that may also be used in embodiments of the present invention include, but are not limited to, bifenox, chlomethoxyfen, fluoroglycofen-ethyl, halosafen, fluazolate, cinidon-ethyl, thidiazimin, oxidiazon, oxadiargyl, azafenidin, pentoxazone, benzfendizone, butafenacid, pyraclinil, profluazol, and/or flufenphyr-ethyl.

Herbicides used in embodiments of the present invention may be used as their free acid or free base forms. Derivatives of herbicdes may also be used, for example herbicides may be used as salts, for example but not limited to sodium salts, and/or esters of the herbicide.

Figure 5:
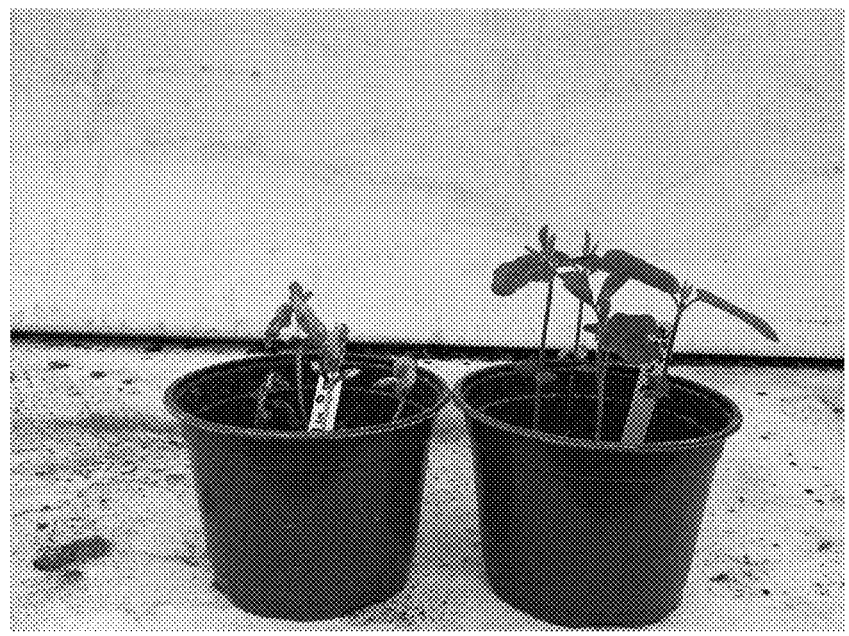
FIG. 5 shows digital images of the safening effect of the mixture of fluridone and flumioxazin in soybean.

In other aspects of applicants work to date, flumioxazin and fomesafen have demonstrated safening effects on fluridone in soybeans. Thus, it has been demonstrated that in plants, such as soybeans, that exhibit significant phytotoxic response to fluridone or other similar bleaching herbicides, a second herbicide can be included to safen the use of the bleaching herbicide. This evidences a very unique safening interaction of fluridone plus PPO-inhibitors by crop species without the interaction causing a similar safening effect on the weed. The second herbicide can be one of those second herbicides identified herein, including more particularly a PPO inhibitor herbicide in some embodiments, or specifically flumioxazin or fomesafen in further embodiments. FIG. 5 illustrates the safening effect of the fluridone and flumioxazin combination on soybean. The pot on left shows that fluridone alone on soybean causes bleaching to the cotyledon. The pot on the right, soybeans were treated with both fluridone and flumioxazin, with the resulting plants having no bleaching, while still maintaining significant weed control.

It has been observed that fluridone may cause chlorosis in soybean plants when used alone. Combinations of fluridone and flumioxazin may reduce the chlorosis observed in soybean plants.

It has also been observed that fomesafen and flumioxazin cause damage to cotton plants when used alone. Also observed was the unexpected benefit that fluridone safens fomesafen when used in combination and that fluridone safens flumioxazin when used in combination on cotton plants.

In still other aspects of the present invention, flumioxazin has been observed to safen fluridone when applied in combination with fluridone to corn plants. In one particular embodiment, flumioxazin was observed to safen fluridone as measured by the percentage of all leaves with visible bleaching injury (% PHYBLE) which is a measure of chlorosis. Compositions and methods that may exhibit this safening affect include, compositions comprising fluridone and/or flumioxazin, and application rates of from about 0.05 pounds per acre (lb/A) to about 0.15 lb/A. In such embodiments, fluridone and/or flumioxazin may be applied separately or together.

Methods and compositions of this disclosure may be used, for example, in the complete or partial control of noxious plants. In certain aspects, these noxious plants include, for example: *Abutilon theophrasti, Acanthospermum hispidum, Acalypha ostrylfolia, Amaranthus albus, Amaranthus hybridus, Amaranthus palmeri, Amaranthus retroflexus, Amaranthus rudis* (waterhemp), *Amaranthus spinosus, Amaranthus*

*tuberculatus, Ambrosia artemisiifolia, Ambrosia trifida, Acalypha ostrylfolia, Anoda cristata, Artemisia biennis, Brachiaria platyphylla, Brassica kaber, Brassica napus, Bromus secalinus, Bromus tectorum, Calandrinia ciliate, Capsella bursa-pastoris, Cassia occidentalis, Cerastium vulgatum, Chenopodium album, Conyza canadensis, Convolvulus arvensis, Croton glandulosus, Cucumis melo, Cyperus iria, Datura stramonium, Descurainia sophia, Descurainia pinnata, Desmodium tortuosum, Digitaria sanguinalis, Digitaria ischaemum, Eclipta prostrate, Echinochloa crus Balli, Eleusine indica, Eragrostis diffusa, Erigeron spp., Erodium cicutarium, Erodium moschatum, Euphorbia maculate, Euphorbia heterophylla, Geranium carolinianum, Hibiscus trionum, Indigofera hirsute, Ipomoea coccinea, Ipomoea hederacea, Ipomoea lacunose, Ipomoea purpurea, Jacquemontia tamnifolia, Kochia scoparia, Lactuca serriola, Lamium amplexicaule, Laminum purpureum, Lolium multiflorum, Malva neglecta, Malva parviflora, Matricaria maritime, Melochia corchorifolia, Mollugo verticillata, Oenothera laciniata, Panicum dichotomiflorum, Panicum texanum, Panicum maximus, Panicum maximum, Plantago major, Poa annua, Polygonum convolvulus, Polygonum lapathifolium, Polygonum pensylvanicum, Polygonum persicaria, Portulaca oleracea, Raphanus raphanistrum, Richardia scabra, Salsola iberica, Senicio glabellus, Senicio vulgaris, Senna obtusifolia, Sesbania exaltata, Setaria faberi, Setaria glauca, Setaria verticillata, Setaria viridis, Sida spinosa, Silene latifolie, Sisymbrium altissimum, Solanum nigrum, Solanum ptycanthum, Solanum sarrachoides, Sonchus oleraceus, Sorghum halepense, Stellaria media, Taraxacum officinale, Trianthema portulacastrum, Tribulus terrestris, Tripleurospermum maritima, Verbesina encelioides, Xanthium strumarium.* In certain aspects, these or other weeds to be controlled can be resistant to glyphosate or other herbicides.

Any herbicide herein can be applied separately in a liquid or solid form, or a combination product containing some or all herbicides can be applied in either liquid or solid form. Typical liquid formulations include emulsions, suspensions (including suspensions containing microcapsules), solutions, emulsifiable concentrates, and flowables. Common solid forms include granules, wettable powders, water-dispersible solids (including water-dispersible granules containing microencapsulated herbicides) or dusts. The herbicidal formulations can also contain, in addition to the active herbicide(s) other ingredients such as adjuvants, surfactants, solvents, wetting agents, suspending agents, anti-caking agents, dispersing agents, emulsifiers, anti-freeze agents, antifoaming agents, and other additives.

Compositions according to this invention may contain the two or more herbicides in numerous different physical forms. In some cases, a composition may be produced by simply physically mixing ("tank mixing") commercially available products containing the active herbicides. Alternatively, a package may be manufactured and sold which contains the two or more herbicides in separate containers, but packaged together, e.g. in a "multi-pack" format such as a "twin-pack" or "tri-pack".

Alternatively, previously prepared compositions ("premixes") containing the two or more herbicides can be produced. Suitable liquid compositions would include solutions or emulsions containing the two or more herbicides. A solid product containing the two or more herbicides could also be produced, for instance, as impregnated granules or flowable powders.

The concentration of the active ingredient or ingredients in the herbicidal compositions of this invention is generally from about 0.001 to about 98 percent by weight. Concentrations from about 0.01 to about 90 percent by weight are often employed. In compositions designed to be employed as concentrates, the active ingredient is generally present in a concentration from about 5 to about 98 weight percent, preferably about 10 to about 90 weight percent. Such compositions are typically diluted with an inert carrier, such as water, before application. The diluted compositions usually applied to weeds or the location of weeds can contain about 0.0001 to about 1 weight percent active ingredient, or about 0.001 to about 0.05 weight percent.

Suitable agricultural adjuvants and carriers that may be useful in preparing the herbicidal mixtures of the invention are well known to those skilled in the art. Liquid carriers that can be used include water, toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methanol, ethanol, isopropanol, amyl alcohol, ethylene glycol, propylene glycol, glycerine, and the like. Water is generally the carrier of choice for the dilution of concentrates. Solid carriers that can be used include talc, pyrophyllite clay, silica, attapulgus clay, kaolin clay, kieselguhr, chalk, diatomaceous earth, lime, calcium carbonate, bentonite clay, Fuller's earth, cottonseed hulls, wheat flour, soybean flour, pumice, wood flour, walnut shell flour, lignin, and the like.

It is usually desirable to incorporate one or more surface-active agents into the compositions of the present invention. Such surface-active agents are advantageously employed in both solid and liquid compositions, especially those designed to be diluted with carrier before application. The surface-active agents can be anionic, cationic or nonionic in character and can be employed as emulsifying agents, wetting agents, suspending agents, or for other purposes. Typical surface-active agents include salts of alkyl sulfates, such as diethanolammonium lauryl sulfate; alkylarylsulfonate salts, such as calciumdodecylbenzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkylnaphthalenesulfonate salts, such as sodium dibutylnaphthalenesulfonate; dialkyl esters of sulfosuccinate salts, such as sodium di(2-ethylhexyl)-sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; and salts of mono and dialkyl phosphate esters.

Other adjuvants commonly used in agricultural compositions include compatibilizing agents, antifoam agents, sequestering agents, neutralizing agents and buffers, corrosion inhibitors, dyes, odorants, spreading agents, penetration aids, sticking agents, dispersing agents, thickening agents, freezing point depressants, antimicrobial agents, and the like. The compositions may also contain other compatible components, for example, other herbicides, plant growth regulators, fungicides, insecticides, and the like and can be formulated with liquid fertilizers or solid, particulate fertilizer carriers such as ammonium nitrate, urea and the like.

In order to promote a further understanding of the present invention and its various embodiments, the following specific examples are provided. It will be understood that these examples are illustrative and not limiting of the invention.

EXAMPLE 1

Greenhouse and Field Efficacy Against Palmer Amaranth and Crop Safety

Materials and Methods:

Field and greenhouse trials were conducted to determine the efficacy and extent of safening of fluridone on fomesafen and flumioxazin.

Cotton was planted in fields in May. The field was then over seeded with *P. amaranth*. On the same day, pre-emergent herbicides were applied at the rates of (1) 0.2 lb/A fluridone; (2) 0.25 lb/A fomesafen; and (3) a combination of 0.2 lb/A fluridone and 0.25 lb/A fomesafen. Within 24 hours of application of the herbicide, 0.25 inches of rain was recorded. An additional planting of cotton, by hand, was conducted in August with multiple rates.

In addition to these field trials, greenhouse studies were also undertaken. The greenhouse studies evaluated the use of fluridone, fomesafen, and the combination of fluridone and fomesafen as well as the affect of soil types, and moisture conditions. Four soil types were examined: a predominantly clay soil, a sandy loam soil, a loamy peat soil, and a sandy soil. The moisture conditions evaluated were at 0.2 inches of water, and 1.5 inches of water.

Results:

All the treatments in the May planting displayed significant control of *P. amaranth* and other weeds compared to the untreated control, however there was no significant difference between the treatments at various concentrations. The weather conditions observed during this trial were ideal for both cotton growth and optimal herbicide efficacy.

In the August planting, the various concentrations of herbicides were tested for phytotoxicity to emerging cotton in a sandy loam soil. Only at the ratio of 0.4 lbs/A of fluridone to 0.4 lbs/A of fomesafen was any phytotoxicity seen, and the phytotoxicity observed at this ratio was minimal. The weather conditions observed during this trial were ideal for both cotton growth and optimal herbicide efficacy. Table 1 describes the conditions used during the greenhouse trials.

There was some variation in weed control which depended on the soil types. For example, under low moisture conditions across some soil types, fomesafen alone was not able to provide complete *P. amaranth* control. Additionally, some stunting was observed in the fomesafen treatments as compared to the fluridone and fluridone/fomesafen combination of treatments, which indicates that the fluridone is able to safen fomesafen under less than ideal growing conditions. Under ideal growing conditions in the greenhouse, all herbicidal applications worked similarly in that no phytotoxicity was observed in the various soil types. However there was some variation in weed control which depended on the soil types. For example, under low moisture conditions across some soil types, fomesafen alone was not able to provide complete *P. Amaranth* control. Additionally, some stunting was observed in the fomesafen treatments as compared to the fluridone and fluridone/fomesafen combination of treatments, which indicates that the fluridone is able to safe and fomesafen under less than ideal growing conditions.

FIG. 1 shows a digital image of the May planting field trials 1 week post treatment and 9 weeks post treatment. Brake is a formulation of fluridone. Brake F2™ is a formulation of fluridone and fomesafen. Fomesafen treatment is also shown. Each treatment showed control of *P. amaranth* and no phytotoxicity was observed in any treatment.

Figure 2:
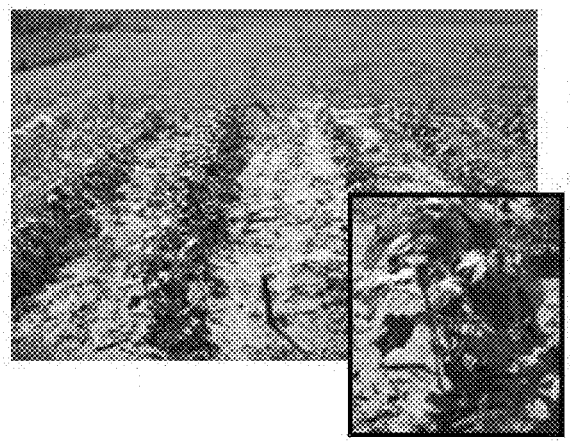
FIG. 2 shows digital images of cotton, taken 7 weeks post treatment. Treatment application was applied by backpack sprayer. At the rate of 0.4:0.4 lbs ai per acre (ai/A) there was phytotoxicity visible on the first true leaves of the cotton, however, plants grew out of this. Plots were overseeded with *P. amaranth* and both ratios completely controlled *P. amaranth* growth in the treated areas. Digital image A shows a field 7 wpt where 0.2:0.2 lb ai per acre fluridone:fomesafen was applied. Digital image B shows a field 7 wpt where 0.4:0.4 lb ai per acre fluridone:fomesafen was applied.
Figure 2:
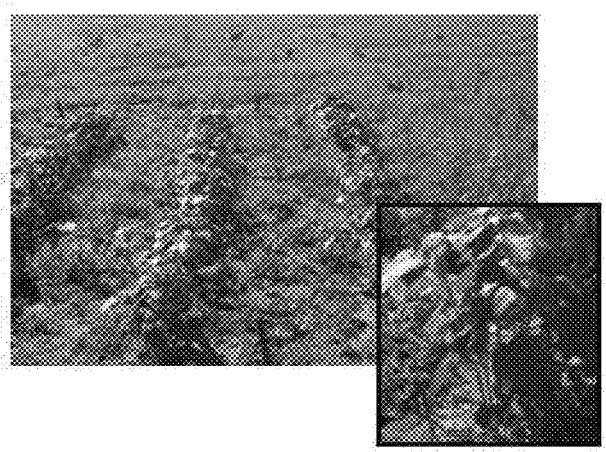

FIG. 2 shows a digital image of the August planting taken 7 weeks post treatment using an application ratio of 0.2 lbs/acre:0.2 lbs/acre fluridone:fomesafen and 0.4 lbs/acre:0.4 lbs/acre fluridone:fomesafen. *P. amaranth* was controlled in both treatment rates and minimal to no phytotoxicity was observed in either application rate. Table 2 summarizes the conditions used during the August field trials.

TABLE 1

Rates used in greenhouse trial examining cotton response across soil types and 2 moisture conditions. Product went out at ratios listed and cotton was examined for phytotoxicity. Fomesafen treatments at a rate of 0.15 lb/A and above exhibited stunting to the cotyledon and first 3 true leaves.

| Plot Number | Herbicide | Herbicide solution concentration (lb/gal) | Application Rate (lb/A) | Ratio of Fluridone to fomesafen |
|---|---|---|---|---|
| 1 | n/a | n/a | n/a | n/a |
| 2 | fluridone | 2 | 0.1 | 1:0 |
| 3 | fluridone | 2 | 0.15 | 1:0 |
| 4 | fluridone | 2 | 0.175 | 1:0 |
| 5 | fluridone | 2 | 0.2 | 1:0 |
| 6 | fluridone/fomesafen | 2 | 0.1 | 1:0.625 |
| 7 | fluridone/fomesafen | 2 | 0.15 | 1:0.625 |
| 8 | fluridone/fomesafen | 2 | 0.175 | 1:0.625 |
| 9 | fluridone/fomesafen | 2 | 0.2 | 1:0.625 |
| 10 | fomesafen | 2 | 0.1 | 0:1 |
| 11 | fomesafen | 2 | 0.15 | 0:1 |
| 12 | fomesafen | 2 | 0.175 | 0:1 |
| 13 | fomesafen | 2 | 0.2 | 0:1 |

TABLE 2

Field rates applied of fluridone and fomesafen in August to cotton. Treatment was applied as a pre-emergent application. *Amaranthus palmeri* was overseeded onto the area. Plots were evaluated for any phytotoxicity to cotton and weed control was evaluated.

| Plot Number | Herbicide | Herbicide solution concentration (lb/gal) | Application Rate (lb/A) | Ratio of Fluridone to fomesafen |
|---|---|---|---|---|
| 1 | n/a | n/a | n/a | n/a |
| 2 | Fluridone | 2 | 0.2 | 1:0 |
| 3 | Fomesafen | 2 | 0.2 | 0:1 |
| 4 | Fluridone | 2 | 0.1 | 1:0.5 |
|   | Fomesafen | 2 | 0.05 |   |
| 5 | Fluridone | 2 | 0.1 | 1:0.75 |
|   | Fomesafen | 2 | 0.075 |   |
| 6 | Fluridone | 2 | 0.1 | 1:1 |
|   | Fomesafen | 2 | 0.1 |   |
| 7 | Fluridone | 2 | 0.15 | 1:0.8 |
|   | Fomesafen | 2 | 0.125 |   |
| 8 | Fluridone | 2 | 0.15 | 1:1 |
|   | Fomesafen | 2 | 0.15 |   |
| 9 | Fluridone | 2 | 0.15 | 1:1.7 |
|   | Fomesafen | 2 | 0.175 |   |
| 10 | Fluridone | 2 | 0.2 | 1:3.75 |
|   | Fomesafen | 2 | 0.75 |   |
| 11 | Fluridone | 2 | 0.2 | 1:0.75 |
|   | Fomesafen | 2 | 0.15 |   |
| 12 | Fluridone | 2 | 0.2 | 1:1 |
|   | Fomesafen | 2 | 0.2 |   |
| 13 | Fluridone | 2 | 0.4 | 1:1 |
|   | Fomesafen | 2 | 0.4 |   |

EXAMPLE 2

Safening of Fluridone by Flumioxazin in Soybeans when Applied Pre-plant

Materials and Methods:

A climate-regulated greenhouse trial was conducted to determine the efficacy and extent of safening of herbicidal compositions of fluridone and flumioxazin applied to soybeans.

In this trial, soybeans were treated with various herbicidal compositions. The quantity of fluridone applied was maintained constant at a rate of 0.2 lb/A and 0.1 b/A fluridone and the quantity of flumioxazin was varied from 0.008 lb/A to 0.17 lb/A flumioxazin. One gallon pots with sandy loam soil were treated with a herbicidal composition, and three soybeans were planted in each pot 7 days after application of the herbicide (i.e., the herbicide was applied 7 days pre-plant) Three pots were prepared and treated for each herbicide composition. Approximately 0.15 inches of water was applied to each pot four hours after application. Irrigation was applied as the plants emerged through the soil 4 days after treatment (DAT) after the first visible signs of soil cracking due to plant emergence was observed. Irrigation comprised application of 0.5 inches of water for 2 days followed by 0.25 inches of water for 2 days, followed by 0.15 inches of water per day for the remainder of the trial. The greenhouse was maintained at 26±5° C. during the day and 11±1° C. during the night.

TABLE 3

Herbicidal compositions applied to soybean plants of EXAMPLE 2.
EXAMPLE 2: Soybean Pre-plant using flumioxazin and fluridone.
Pre-emergent and Pre Plant Applications of fluridone in combination with flumioxazin on Soybean
Trial ID: 20140117.1 BH Protocol ID: 20140117.1 BH

| Trt No. | Treatment Name | Form Conc | Form Unit | Form Type | Description | Rate | Rate Unit |
|---|---|---|---|---|---|---|---|
| 1 | Flumioxazin | 51.00 | % | WG | 7 Day | 8 | oz/a |
| 2 | Fluridone | 2 | LB/GAL | EC | 7 Day | 0.05 | lb ai/a |
|  | Flumioxazin | 51.00 | % | WG | 7 Day | 0.255 | lb ai/a |
| 3 | Fluridone | 2 | LB/GAL | EC | 7 Day | 0.10 | lb ai/a |
|  | Flumioxazin | 51.00 | % | WG | 7 Day | 0.255 | lb ai/a |
| 4 | Fluridone | 2 | LB/GAL | EC | 7 Day | 0.20 | lb ai/a |
|  | Flumioxazin | 51.00 | % | WG | 7 Day | 0.255 | lb ai/a |
| 5 | Fluridone | 2 | LB/GAL | EC | 7 Day | 0.03 | lb ai/a |
|  | Flumioxazin | 51.00 | % | WG | 7 Day | 0.255 | lb ai/a |
| 6 | Flumioxazin | 51.00 | % | WG | 7 Day | 0.17 | lb ai/a |
| 7 | Fluridone | 2 | LB/GAL | EC | 7 Day | 0.05 | lb ai/a |
|  | Flumioxazin | 51.00 | % | WG | 7 Day | 0.17 | lb ai/a |
| 8 | Fluridone | 2 | LB/GAL | EC | 7 Day | 0.10 | lb ai/a |
|  | Flumioxazin | 51.00 | % | WG | 7 Day | 0.17 | lb ai/a |
| 9 | Fluridone | 2 | LB/GAL | EC | 7 Day | 0.20 | lb ai/a |
|  | Flumioxazin | 51.00 | % | WG | 7 Day | 0.17 | lb ai/a |
| 10 | Fluridone | 2 | LB/GAL | EC | 7 Day | 0.03 | lb ai/a |
|  | Flumioxazin | 51.00 | % | WG | 7 Day | 0.17 | lb ai/a |
| 11 | Flumioxazin | 51.00 | % | WG | 7 Day | 0.128 | lb ai/a |
| 12 | Fluridone | 2 | LB/GAL | EC | 7 Day | 0.05 | lb ai/a |
|  | Flumioxazin | 51.00 | % | WG | 7 Day | 0.128 | lb ai/a |
| 13 | Fluridone | 2 | LB/GAL | EC | 7 Day | 0.10 | lb ai/a |
|  | Flumioxazin | 51.00 | % | WG | 7 Day | 0.128 | lb ai/a |
| 14 | Fluridone | 2 | LB/GAL | EC | 7 Day | 0.20 | lb ai/a |
|  | Flumioxazin | 51.00 | % | WG | 7 Day | 0.128 | lb ai/a |
| 15 | Fluridone | 2 | LB/GAL | EC | 7 Day | 0.03 | lb ai/a |
|  | Flumioxazin | 51.00 | % | WG | 7 Day | 0.128 | lb ai/a |
| 16 | Flumioxazin | 51.00 | % | WG | 7 Day | 0.016 | lb ai/a |
| 17 | Fluridone | 2 | LB/GAL | EC | 7 Day | 0.10 | lb ai/a |
|  | Flumioxazin | 51.00 | % | WG | 7 Day | 0.016 | lb ai/a |
| 18 | Fluridone | 2 | LB/GAL | EC | 7 Day | 0.20 | lb ai/a |
|  | Flumioxazin | 51.00 | % | WG | 7 Day | 0.016 | lb ai/a |
| 19 | Flumioxazin | 51.00 | % | WG | 7 Day | 0.008 | lb ai/a |
| 20 | Fluridone | 2 | LB/GAL | EC | 7 Day | 0.10 | lb ai/a |
|  | Flumioxazin | 51.00 | % | WG | 7 Day | 0.008 | lb ai/a |
| 21 | Fluridone | 2 | LB/GAL | EC | 7 Day | 0.20 | lb ai/a |
|  | Flumioxazin | 51.00 | % | WG | 7 Day | 0.008 | lb ai/a |
| 22 | UTC |  |  |  | 7 Day |  |  |

Figure 6:
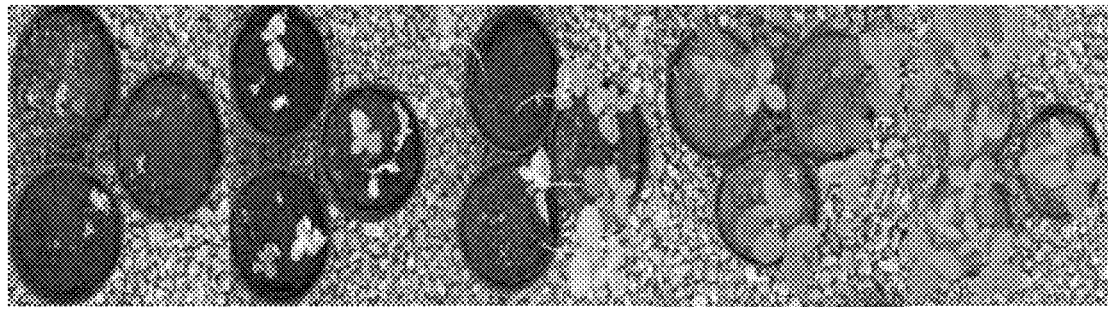
FIG. 6 shows digital images of soybean plants treated with various quantites of fluridone and flumioxazin when applied pre-plant. 6.1. is 0.2 lb/A fluridone+0.008 lb/A of flumioxazin. 6.2. is 0.2 lb/A fluridone+0.016 lb/A of flumioxazin. 6.3. is 0.2 lb/A fluridone+0.125 lb/A of flumioxazin. 6.4. is 0.2 lb/A fluridone+0.17 lb/A of flumioxazin. 6.5. is untreated control (UTC).

Results:

FIG. 6 shows a series of five digital images of soybeans planted during the trial. In the first image from the left, a herbicidal composition comprising 0.2 lb/A fluridone and 0.008 lb/A of flumioxazin was applied to the plant; in the second digital image 0.2 lb/A fluridone and 0.016 lb/A flumioxazin was applied; in the third digital image 0.2 lb/A fluridone and 0.128 lb/A flumioxazin was applied; in the fourth digital image, 0.2 lb/A fluridone and 0.17 lb/A flumioxazin was applied; in the fifth digital image, no herbicidal compositions were applied and used an untreated control.

Figure 7:
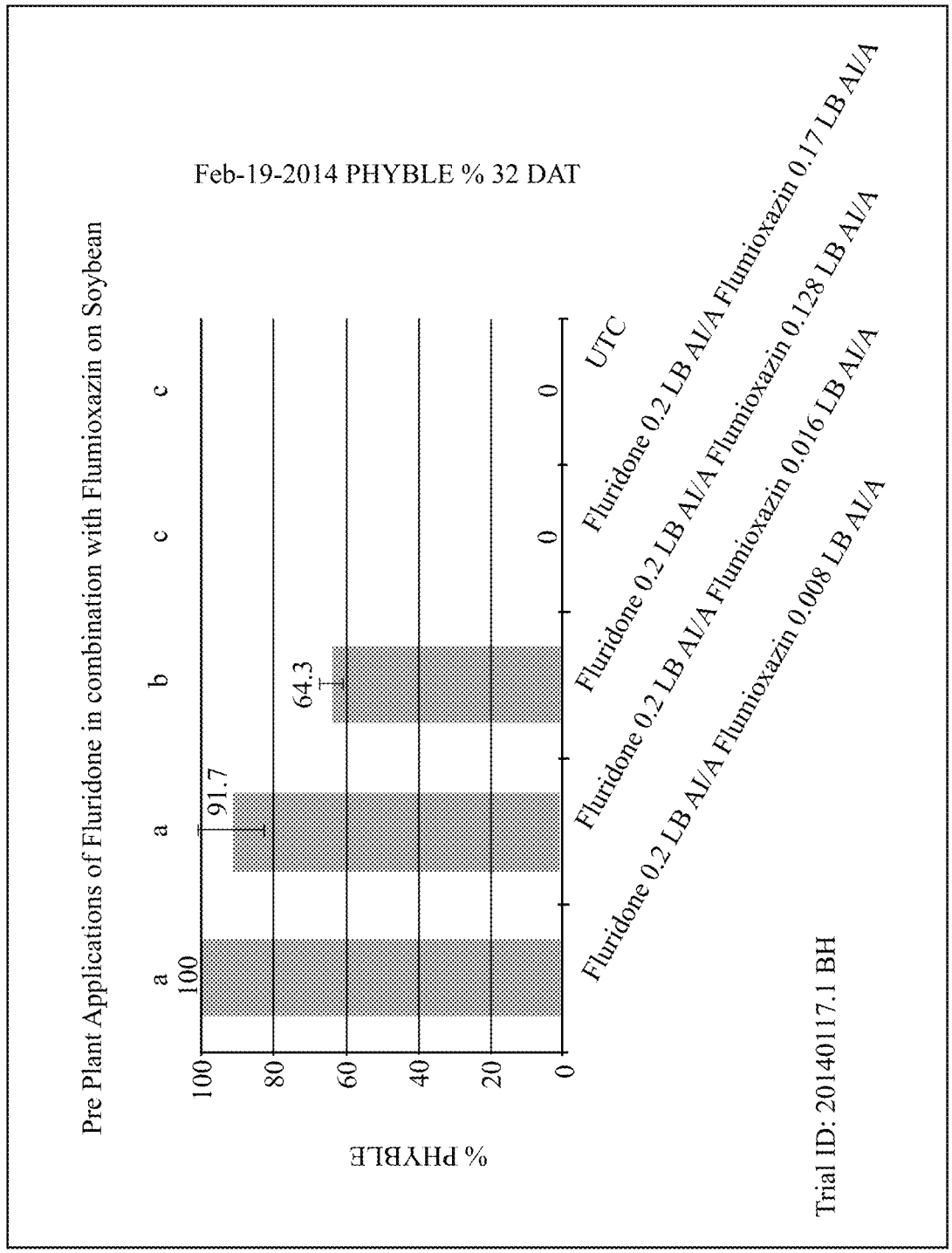
FIG. 7 show the percentage of chlorosis observed on soybean plants treated with fluridone and flumioxazin when applied pre-plant. UTC is untreated control.

FIG. 7 shows a graph of the percent chlorosis (PHYBLE) observed on the soybean plants of the present trial. The untreated control soybean plants exhibited 0% chlorosis. Soybeans treated with 0.2 lb/A fluridone in combination with the smallest rate of flumioxazin, 0.008 lb/A flumioxazin, exhibited 100% chlorosis and was fatal to the soybean plants. Chlorosis decreased as the rate of flumioxazin increased. Soybeans treated with 0.2 lb/A fluridone in combination with the largest rate of flumioxazin, 0.17 lb/A flumioxazin, exhibited 0% chlorosis. These data evidences that flumioxazin safens soybeans against the application of fluridone when applied pre-plant.

Figure 8:
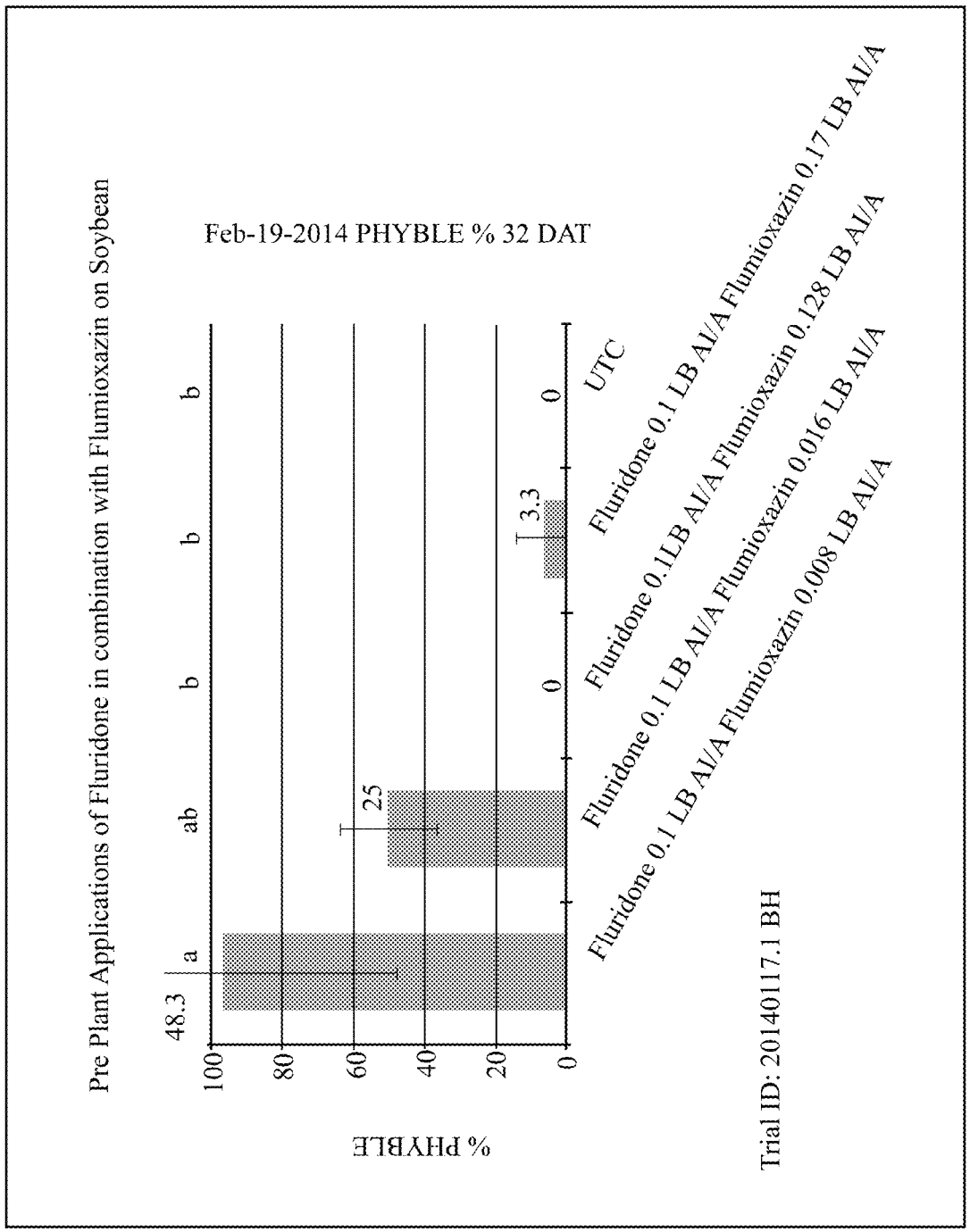
FIG. 8 shows the percentage of leaves including cotyledon, unifolate, and/or trifoliate leaves with visible bleaching observed on soybean plants treated with fluridone and flumioxazin when applied pre-plant.

A similar trend is observed in FIG. 8. The untreated control soybean plants exhibited 0% chlorosis. Soybeans treated with 0.1 lb/A fluridone in combination with the smallest rate of flumioxazin, 0.008 lb/A flumioxazin, exhibited 48.3% chlorosis. Chlorosis generally decreased as the rate of flumioxazin increased. Soybeans treated with 0.1 lb/A fluridone in combination with the largest does of flumioxazin, 0.17 lb/A flumioxazin, exhibited only 3.3% chlorosis. These data also evidence that flumioxazin safens soybeans against the application of fluridone when applied pre-plant.

EXAMPLE 3

Pre-emergent Application of Combinations of Fluridone with Flumioxazin or Fomesafe in Cotton and Soybeans A trial was conducted in a climate-controlled growth chamber to determine the efficacy and extent of safening of combinations of fluridone with flumioxazin or fluridone with fomesafen on soybeans and cotton.

0.1 L conical assay tubes were planted with a cotton or soybean seed in a sample of sandy loam soil. Seven tubes were prepared for each herbicide application rate. Application of a herbicide composition was performed after planting the seed and prior to the plant's emergence from the soil (i.e., pre-emergent or PRE). Approximately 0.15 inches of water was applied to each pot four hours after application. Irrigation was applied as the plants emerged through the soil 4 days after treatment (DAT) after the first visible signs of soil cracking due to plant emergence was observed. Irrigation comprised application of 0.5 inches of water for 2 days followed by 0.25 inches of water for 2 days, followed by 0.15 inches of water per day for the remainder of the trial. The greenhouse was maintained at 26±5° C. during the day and 11±1° C. during the night.

Table 4 shows the herbicidal compositions applied to soybean plants of the present example.

TABLE 4

Herbicidal compositions applied to soybean plants of EXAMPLE 3.
EXAMPLE 3: Pre-emergent Applications of Brake, Reflex, and Valor on Soybean to Evaluate Injury Under Cool and Moist Conditions
Trial ID: 20140203.2 Protocol ID: 20140203.2

| Trt No. | Treatment Name | Form Conc | Form Unit | Form Type | Rate | Rate Unit |
|---|---|---|---|---|---|---|
| 1 | Fluridone | 2 | LBA/GAL | EC | 0.025 | lb ai/a |
| 2 | Fluridone | 2 | LBA/GAL | EC | 0.05 | lb ai/a |
| 3 | Fluridone | 2 | LBA/GAL | EC | 0.1 | lb ai/a |
| 4 | Fluridone | 2 | LBA/GAL | EC | 0.2 | lb ai/a |
| 5 | Fomesafen | 2 | LBA/GAL | EC | 0.125 | lb ai/a |
| 6 | Fomesafen | 2 | LBA/GAL | EC | 0.25 | lb ai/a |
| 7 | Fomesafen | 2 | LBA/GAL | EC | 0.375 | lb ai/a |
| 8 | Fomesafen | 2 | LBA/GAL | EC | 0.5 | lb ai/a |
| 9 | Flumioxazin | 51 | % | WG | 1.5 | oz/a |
| 10 | Flumioxazine | 51 | % | WG | 3 | oz/a |
| 11 | Flumioxazine | 51 | % | WG | 6 | oz/a |
| 12 | Flumioxazin | 51 | % | WG | 9 | oz/a |
| 13 | Fluridone | 2 | LBA/GAL | EC | 0.025 | lb ai/a |
|  | Fomesafen | 2 | LBA/GAL | EC | 0.5 | lb ai/a |
| 14 | Fluridone | 2 | LBA/GAL | EC | 0.05 | lb ai/a |
|  | Fomesafen | 2 | LBA/GAL | EC | 0.5 | lb ai/a |
| 15 | Fluridone | 2 | LBA/GAL | EC | 0.1 | lb ai/a |
|  | Fomesafen | 2 | LBA/GAL | EC | 0.5 | lb ai/a |
| 16 | Fluridone | 2 | LBA/GAL | EC | 0.1 | lb ai/a |
|  | Flumioxazin | 51 | % | WG | 1.5 | oz/a |
| 17 | Fluridone | 2 | LBA/GAL | EC | 0.1 | lb ai/a |
|  | Flumioxazin | 51 | % | WG | 3 | oz/a |
| 18 | UTC |  |  |  |  |  |

Table 5 shows the herbicidal compositions applied to cotton plants of the present example.

TABLE 5

Herbicidal compositions applied to cotton plants of EXAMPLE 3.
EXAMPLE 3: Pre-emergent Applications of Brake, Reflex, and Valor on Cotton to Evaluate Injury Under Cool and Moist Conditions
Trial ID: 20140203.1 Protocol ID: 20140203.1

| Trt No. | Treatment Name | Form Conc | Form Unit | Form Type | Rate | Rate Unit |
|---|---|---|---|---|---|---|
| 1 | Fluridone | 2 | LBA/GAL | EC | 0.05 | lb ai/a |
| 2 | Fluridone | 2 | LBA/GAL | EC | 0.1 | lb ai/a |
| 3 | Fluridone | 2 | LBA/GAL | EC | 0.2 | lb ai/a |
| 4 | Fluridone | 2 | LBA/GAL | EC | 0.4 | lb ai/a |
| 5 | Fomesafen | 2 | LBA/GAL | EC | 0.125 | lb ai/a |
| 6 | Fomesafen | 2 | LBA/GAL | EC | 0.25 | lb ai/a |
| 7 | Fomesafen | 2 | LBA/GAL | EC | 0.375 | lb ai/a |
| 8 | Fomesafen | 2 | LBA/GAL | EC | 0.5 | lb ai/a |
| 9 | Flumioxazin | 51 | % | WG | 0.0125 | oz/a |
| 10 | Flumioxazin | 51 | % | WG | 0.025 | oz/a |
| 11 | Flumioxazin | 51 | % | WG | 0.075 | oz/a |
| 12 | Flumioxazin | 51 | % | WG | 0.1 | oz/a |
| 13 | Fluridone | 2 | LBA/GAL | EC | 0.1 | lb ai/a |
|  | Fomesafen | 2 | LBA/GAL | EC | 0.25 | lb ai/a |
| 14 | Fluridone | 2 | LBA/GAL | EC | 0.2 | lb ai/a |
|  | Fomesafen | 2 | LBA/GAL | EC | 0.25 | lb ai/a |
| 15 | Fluridone | 2 | LBA/GAL | EC | 0.4 | lb ai/a |
|  | Fomesafen | 2 | LBA/GAL | EC | 0.25 | lb ai/a |
| 16 | Fluridone | 2 | LBA/GAL | EC | 0.2 | lb ai/a |
|  | Flumioxazin | 51 | % | WG | 0.075 | oz/a |
| 17 | Fluridone | 2 | LBA/GAL | EC | 0.4 | lb ai/a |
|  | Flumioxazin | 51 | % | WG | 0.075 | oz/a |
| 18 | UTC |  |  |  |  |  |

Figure 9:
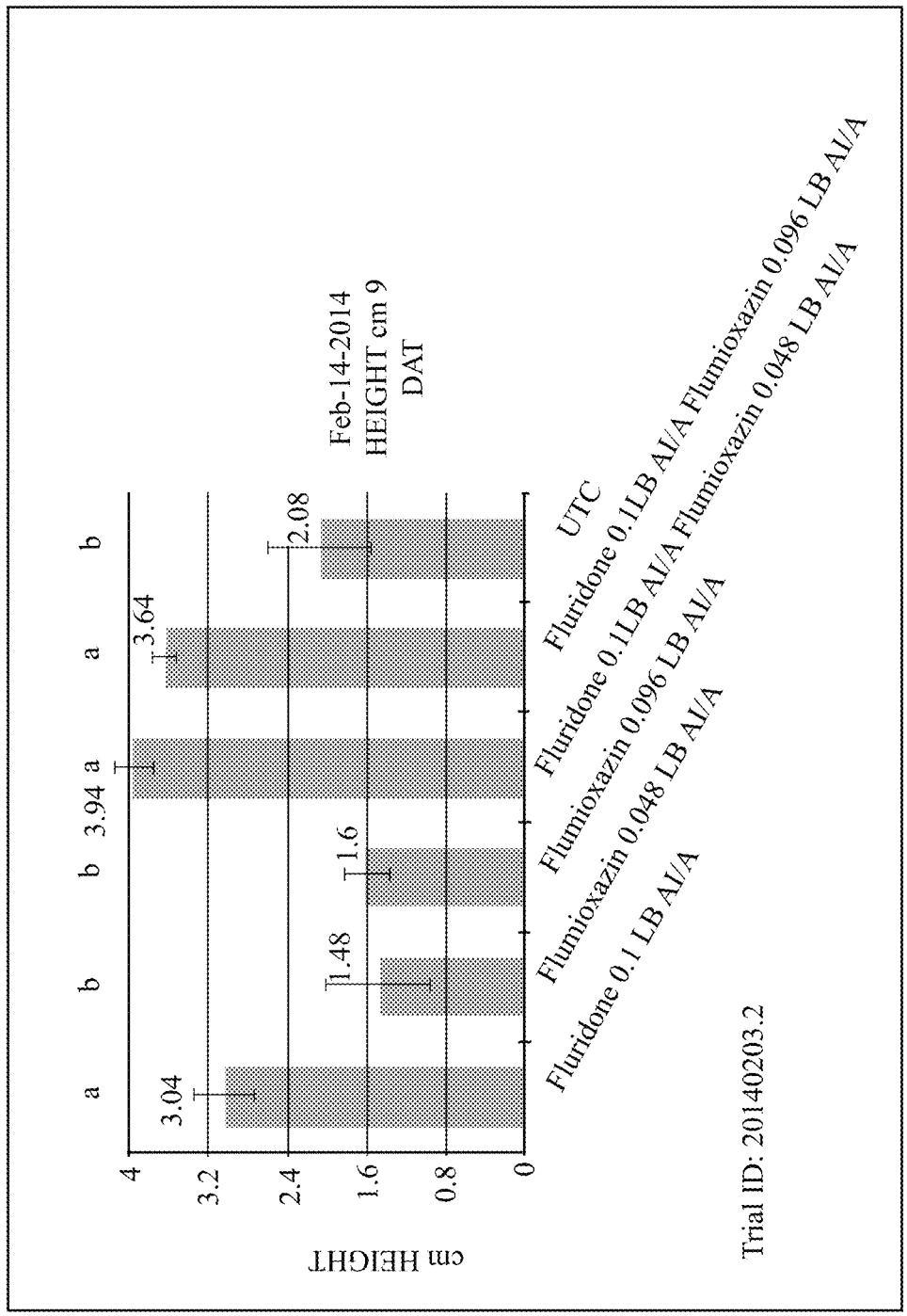
FIG. 9 shows the height of soybean plants 9 days after treatment with herbicide compositions comprising fluridone; flumioxazin; as well as compositions with various ratios of fluridone and flumioxazin.

Soybeans:

FIG. 9 shows the height of soybean plants 9 days after treatment with a herbicide compositions comprising fluridone; flumioxazin; and various ratios of fluridone and flumioxazin.

Figure 10:
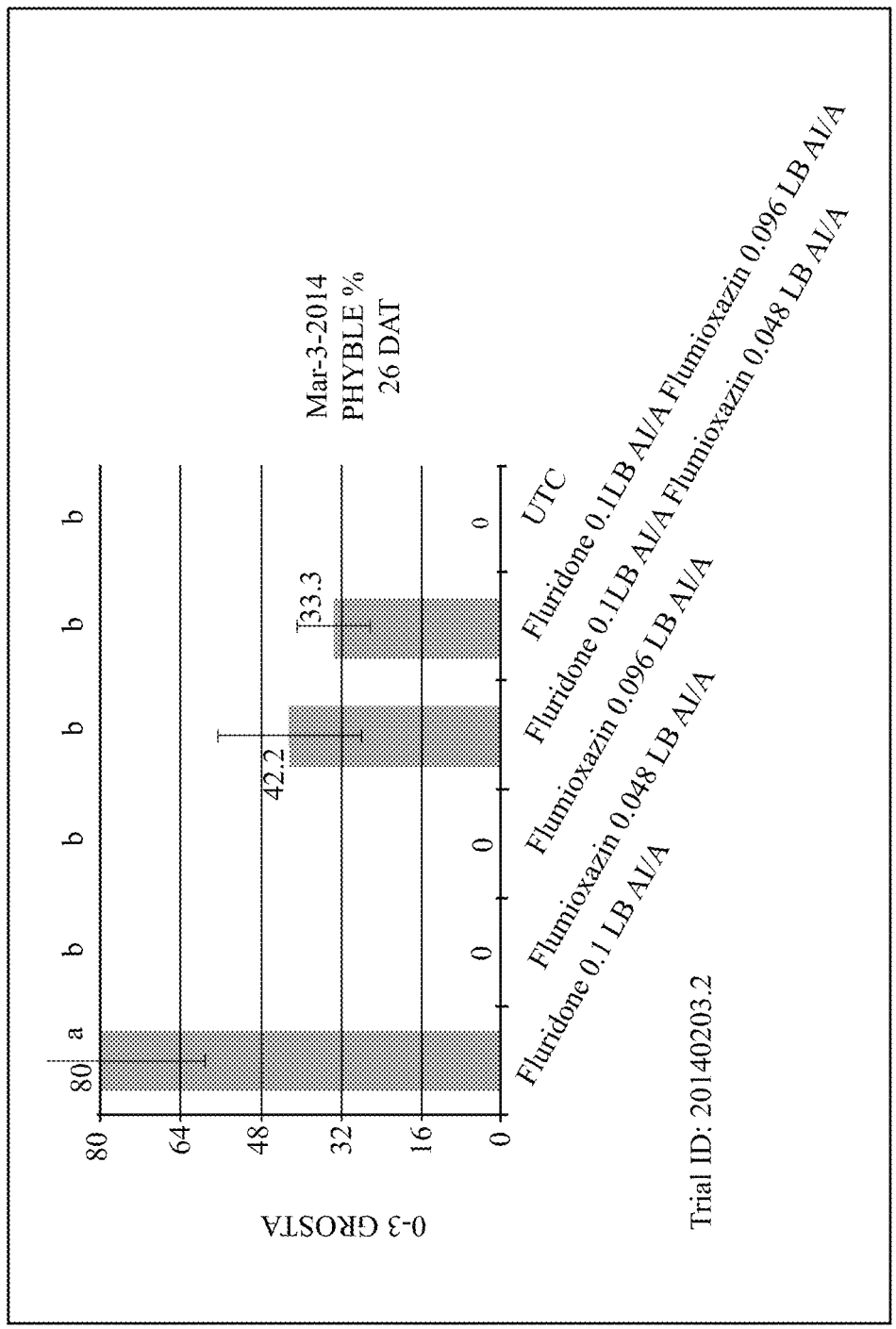
FIG. 10 shows the percentage of chlorosis observed in soybean plants treated with herbicidal compositions.

FIG. 10 shows the percentage of chlorosis observed in soybean plants treated with various herbicidal compositions. For example, when soybean plants were treated with fluridone, 80% chlorosis was observed. When a herbicidal composition comprising fluridone and flumioxazin was applied, the percentage chlorosis observed decreased. These data evidence that when fluridone and flumioxazin are used in combination, increasing rates of flumioxazin decreases the quantity of chlorosis observed on soybeans.

Figure 11:
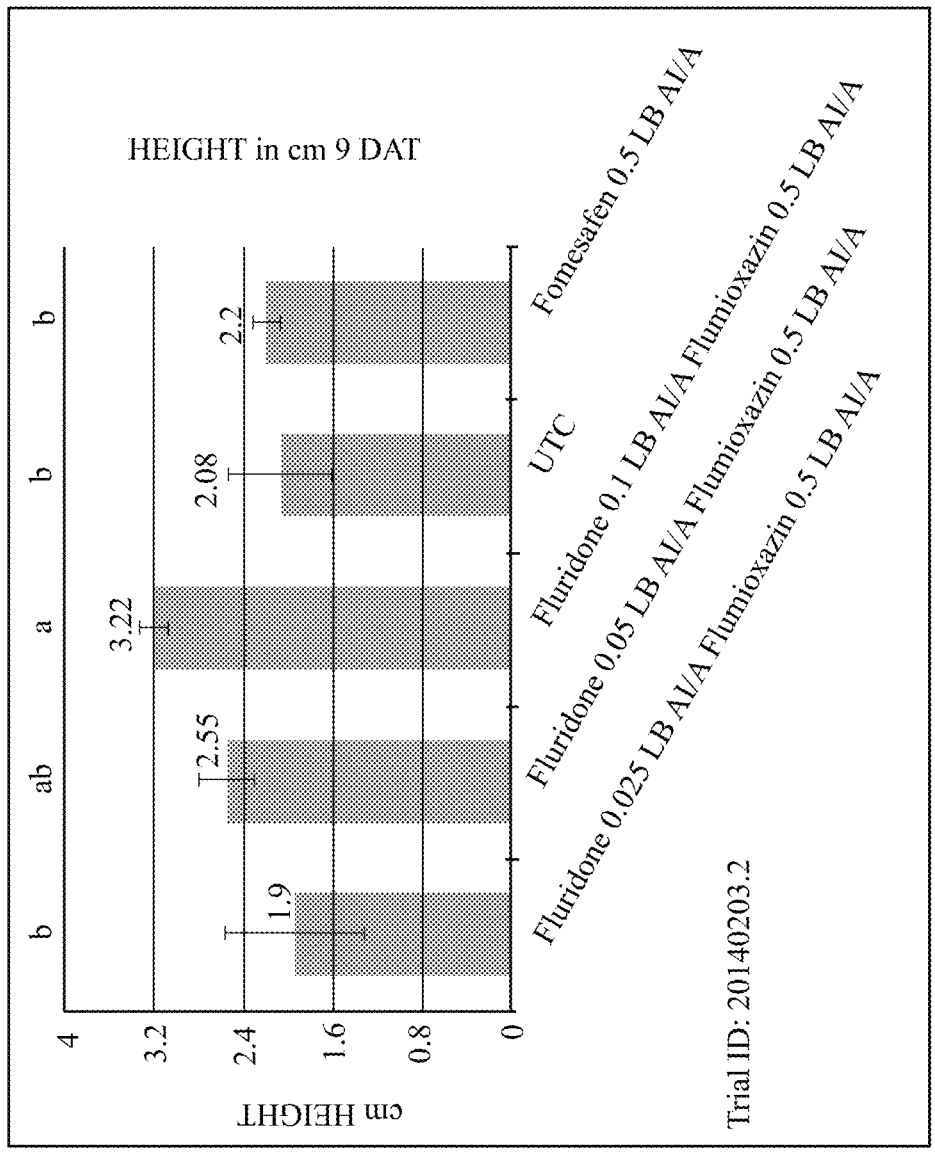
FIG. 11 shows the percentage of chlorosis observed in soybean plants treated with herbicidal compositions.

FIG. 11 shows the percentage of chlorosis observed in soybean plants treated with various herbicidal compositions. For example, when soybean plants were treated with fluridone and fomesafen a decrease in chlorosis was not observed in contrast to the decrease of chlorosis observed with fluridone and flumioxazin are used in combination.

These data evidence that when fluridone and flumioxazin are used in combination, a safening affect is observed on soybean plants as measured by percent chlorosis observed. When fluridone and fomesafen are used in combination a safening affect is not observed on soybean plants as measured by percent chlorosis observed.

Figure 12:
FIG. 12 shows digital images of cotton plants 16 days after treatment with herbicidal compositions comprising fluridone and fomesafen. 12.1 is untreated (UTC). 12.2 is 0.25 lb ai/a fomesafen. 12.3 is 0.1 ai/A fluridone+0.25 lb ai/A fomesafen.

Cotton:

FIG. 12 show digital images of cotton plants 16 days after treatment with herbicidal compositions comprising fluridone and fomesafen. Generally speaking, the crop phytotoxicity and growth inhibition caused by fomesafen alone was improved by the use of a combination of fluridone and fomesafen. Starting from the left, the first plant is a cotton plant that was not treated with a herbicidal composition. The middle plant is a cotton plant treated with 0.25 lb/A of fomesafen. The plant on the right is a cotton plant treated with 0.25 lb/A of fomesafen in combination with fluridone.

Figure 13:
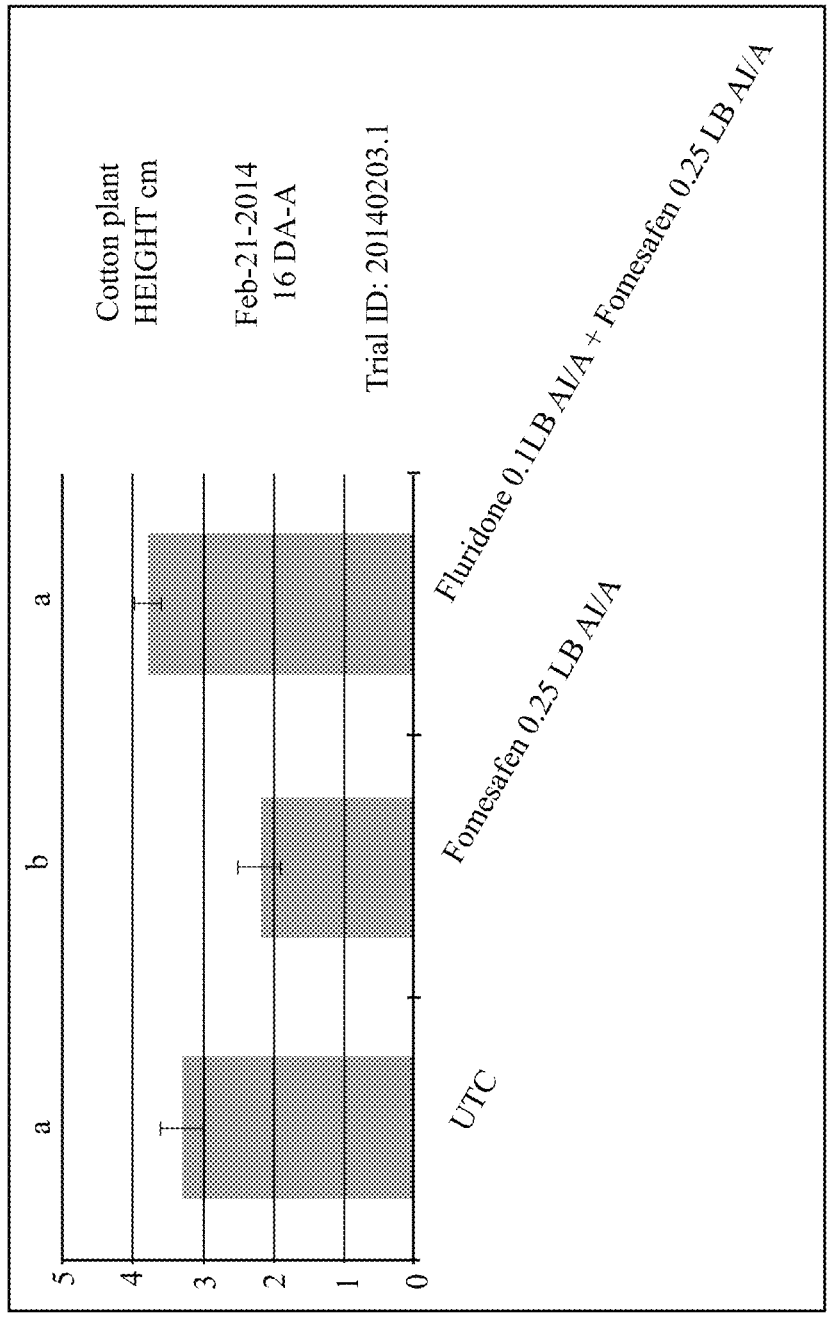
FIG. 13 shows the height of cotton plants 16 days after treatment with herbicidal compositions.

FIG. 13 shows the height of cotton plants 16 days after treatment with a herbicidal composition. Shown are untreated control plants, plants treated with 0.25 lb/A fomesafen, and plants treated with a combination of 0.1 lb/A fluridone and 0.25 lb/A fomesafen.

Figure 14:
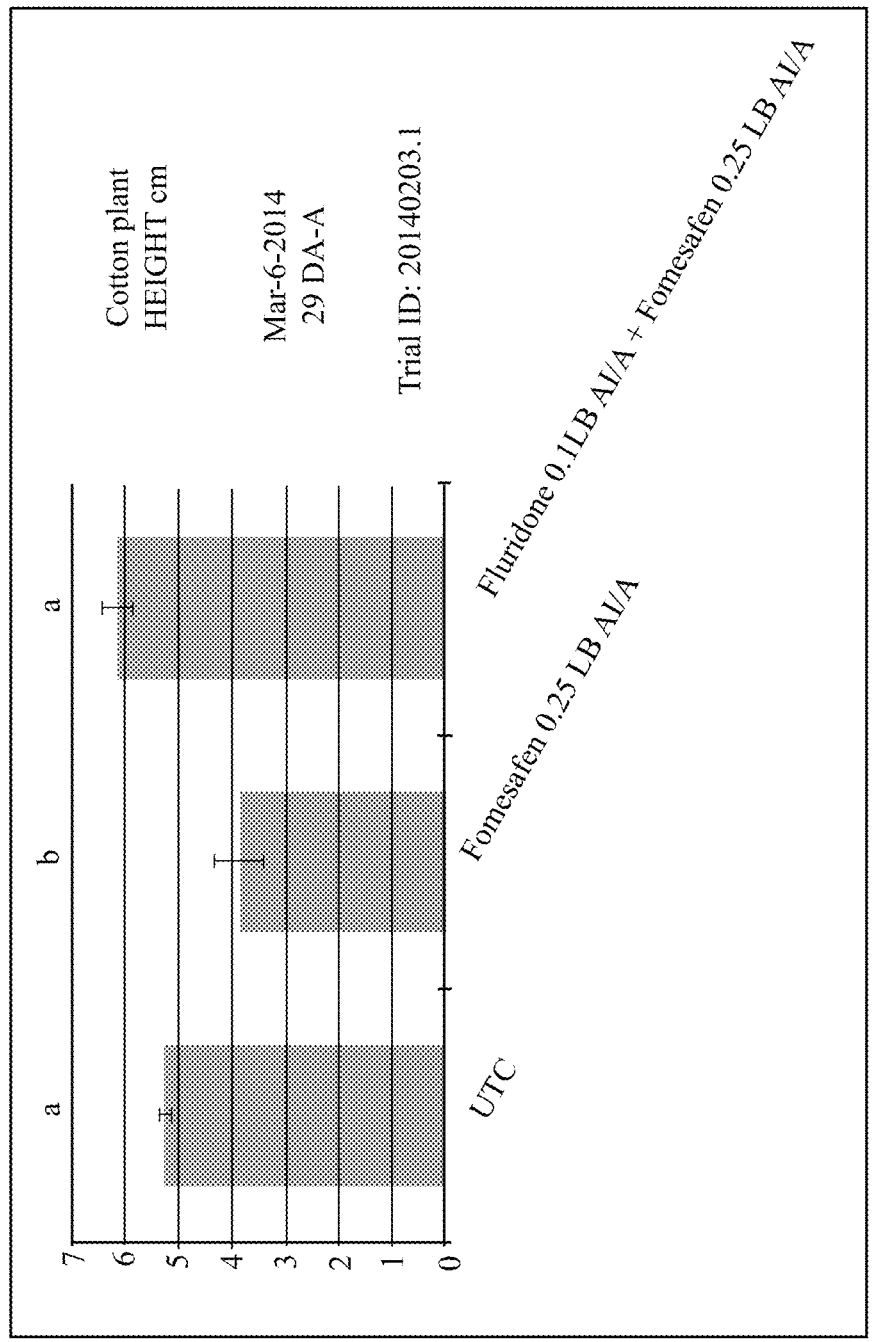
FIG. 14 shows the height of cotton plants 29 days after treatment with herbicidal compositions.

FIG. 14 shows the height of cotton plants 29 days after treatment with a herbicidal composition. Shown are untreated control plants, plants treated with 0.25 lb/A fomesafen, and plants treated with a combination of 0.1 lb/A fluridone and 0.25 lb/A fomesafen.

These data evidence that cotton plants treated with a combination of fluridone and fomesafen exhibit less phytotoxicity and growth inhibition than plants treated only with fluridone.

Figure 15:
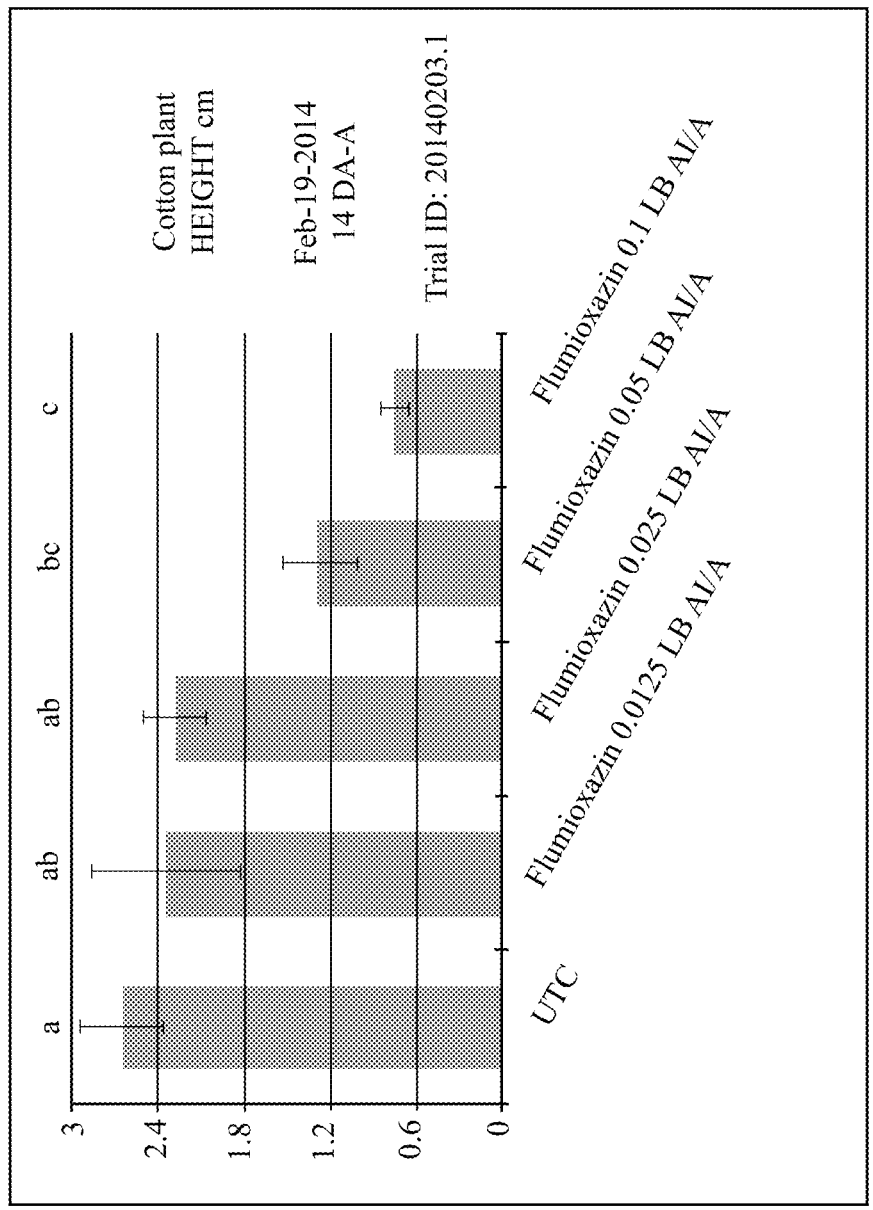
FIG. 15 shows the height of cotton plants treated with various rates of flumioxazin.

FIG. 15 shows the height of cotton plants treated with various rates of flumioxazin. As can be seen from the bar graph, as the rate of flumioxazin is increased, the height of cotton plants decrease. At the highest rates, flumioxazin was fatal to cotton plants. At application rates greater than 0.025 lb/A flumioxazin, cotton plants were significantly injured.

Figure 16:
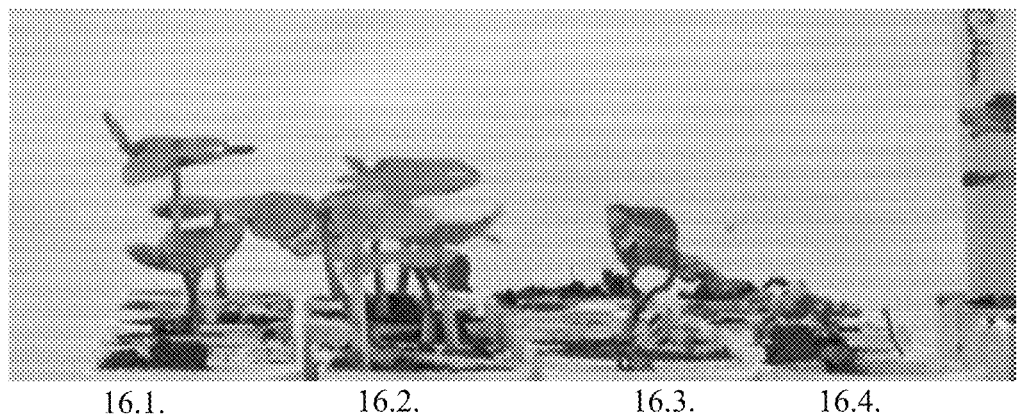
FIG. 16 shows digital images of cotton plants treated with flumioxazin. 16.1. is 0.0125 lb ai/A flumioxazin. 16.2. is 0.025 lb ai/A flumioxazin. 16.3. is 0.05 lb ai/A flumioxazin. 16.4. is 0.1 lb ai/A flumioxazin.

FIG. 16 shows digital images of cotton plants treated with flumioxazin. As the rate of flumioxazin increases, the height of the cotton plants decreases.

Figure 17:
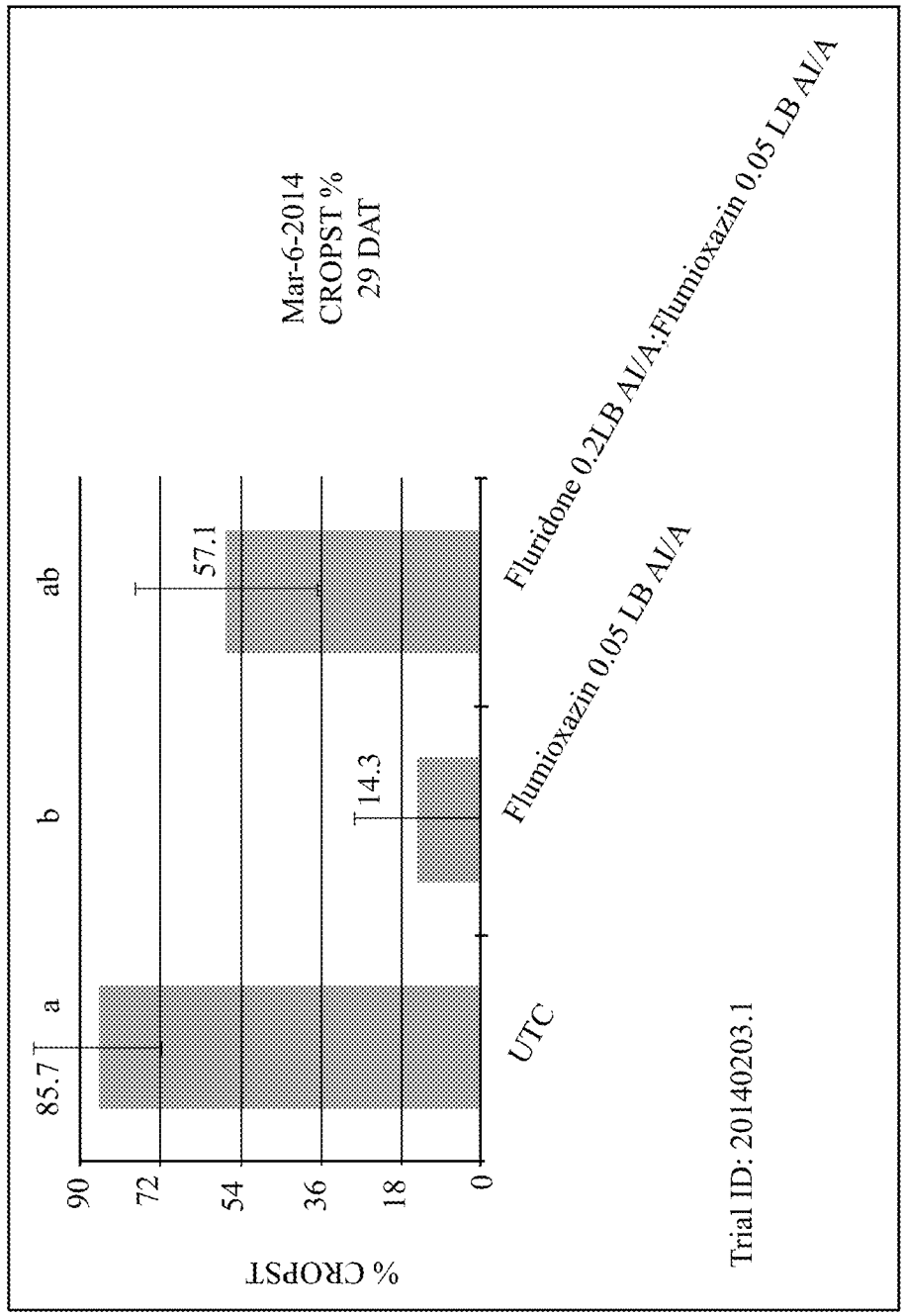
FIG. 17 shows the crop stand, which is the number of viable plants, for cotton plants treated with herbicidal compositions.

FIG. 17 shows the crop stand, which is the number of viable plants, for cotton plants treated with 0.5 lb/A flumioxazin, 0.2 lb/A fluridone plus 0.05 lb/A flumioxazin, as well as plants that went untreated as a control. The crop stand was one surviving plants out of seven for cotton plants treated with 0.05 lb/A flumioxazin. The crop stand was four surviving plants out of seven cotton plants treated with 0.2 lb/A fluridone.

Figure 18:
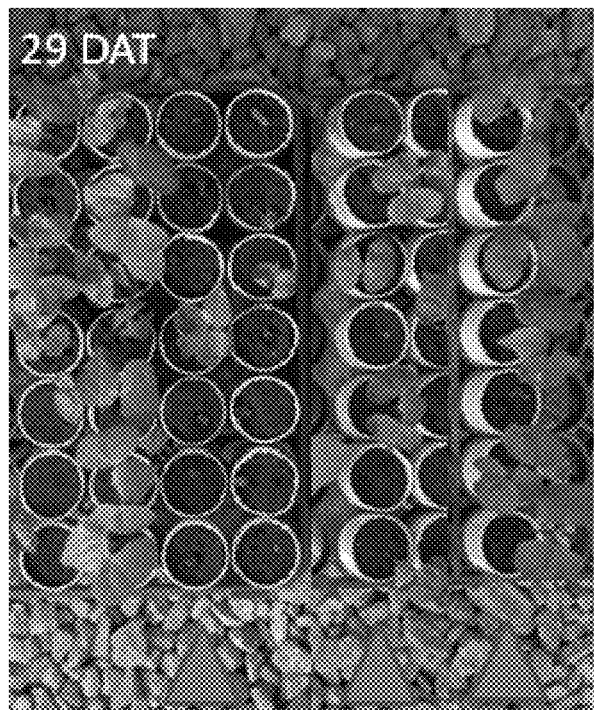
FIG. 18 shows a digital image where cotton plants were various treatments were applied to cotton plants. One set of cotton plants were treated with flumioxazin at the rate of 0.05 lb/A, (18.1.), one set of plants was treated with a combination of flumioxazin at 0.05 lb/A and fluridone at 0.2 lb/A (18.2.), and one set was left untreated as an untreated control (18.3., UTC).

FIG. 18 shows a digital image where cotton plants were various treatments were applied to cotton plants. One set of cotton plants were treated with flumioxazin at the rate of 0.05 lb/A, one set of plants was treated with a combination of flumioxazin at 0.05 lb/A and fluridone at 0.2 lb/A, and one set was left untreated as an untreated control (UTC).

Figure 19:
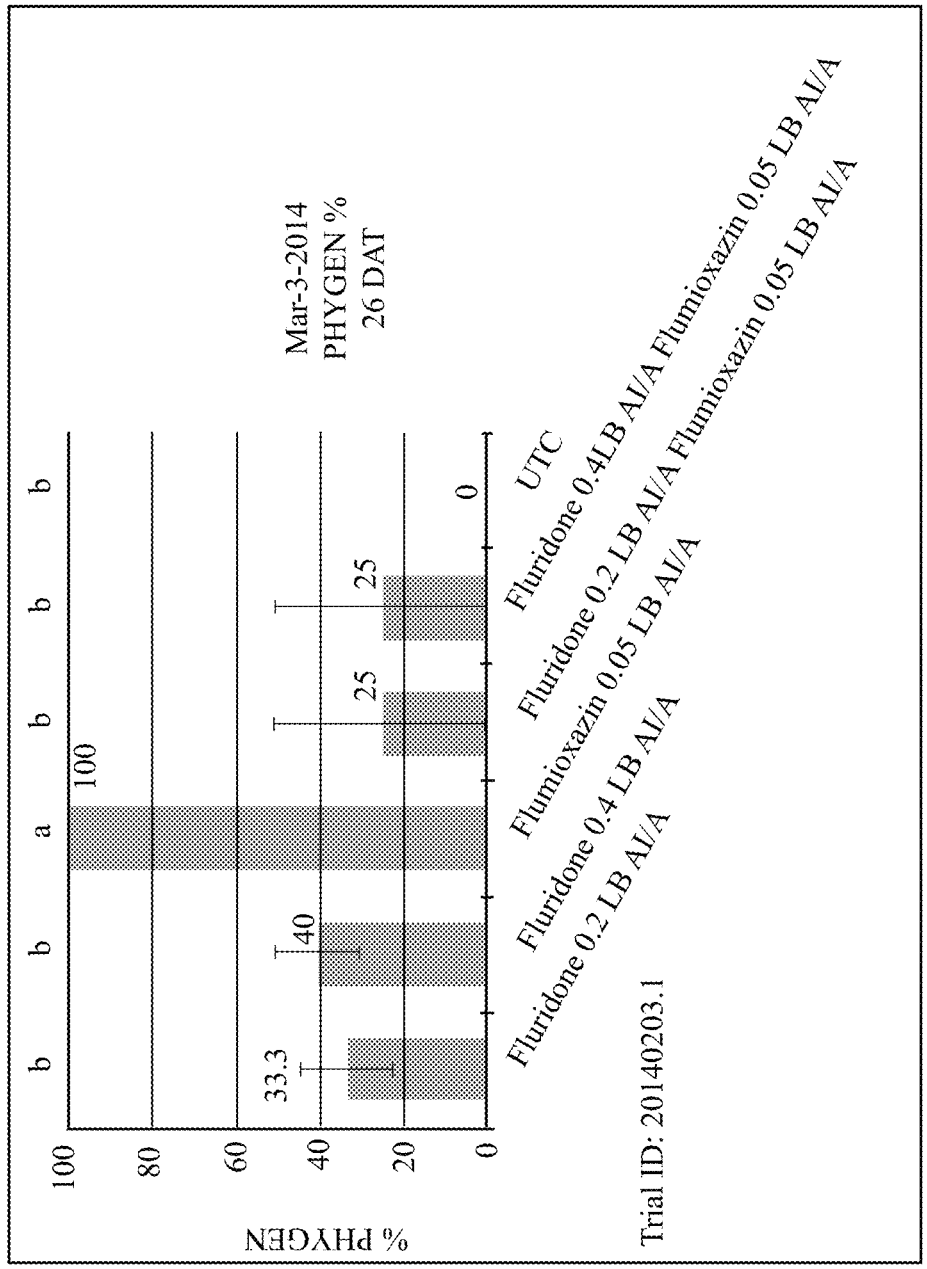
FIG. 19 shows the percentage of cotyledons with excessive wrinkling and brown spotting due to herbicide injury measured 26 days after treatment.

FIG. 19 shows the percentage of cotyledons with excessive wrinkling and brown spotting due to herbicide injury measured 26 days after treatment. As shown here, when flumioxazin is used alone at the rate of 0.05 lb/A all of the cotyledons show brown spotting. When fluridone is added at the rate of 0.2 lb/A or 0.4 lb/A, the number of cotyledons that have brown spots decreases by 75%.

Figure 20:
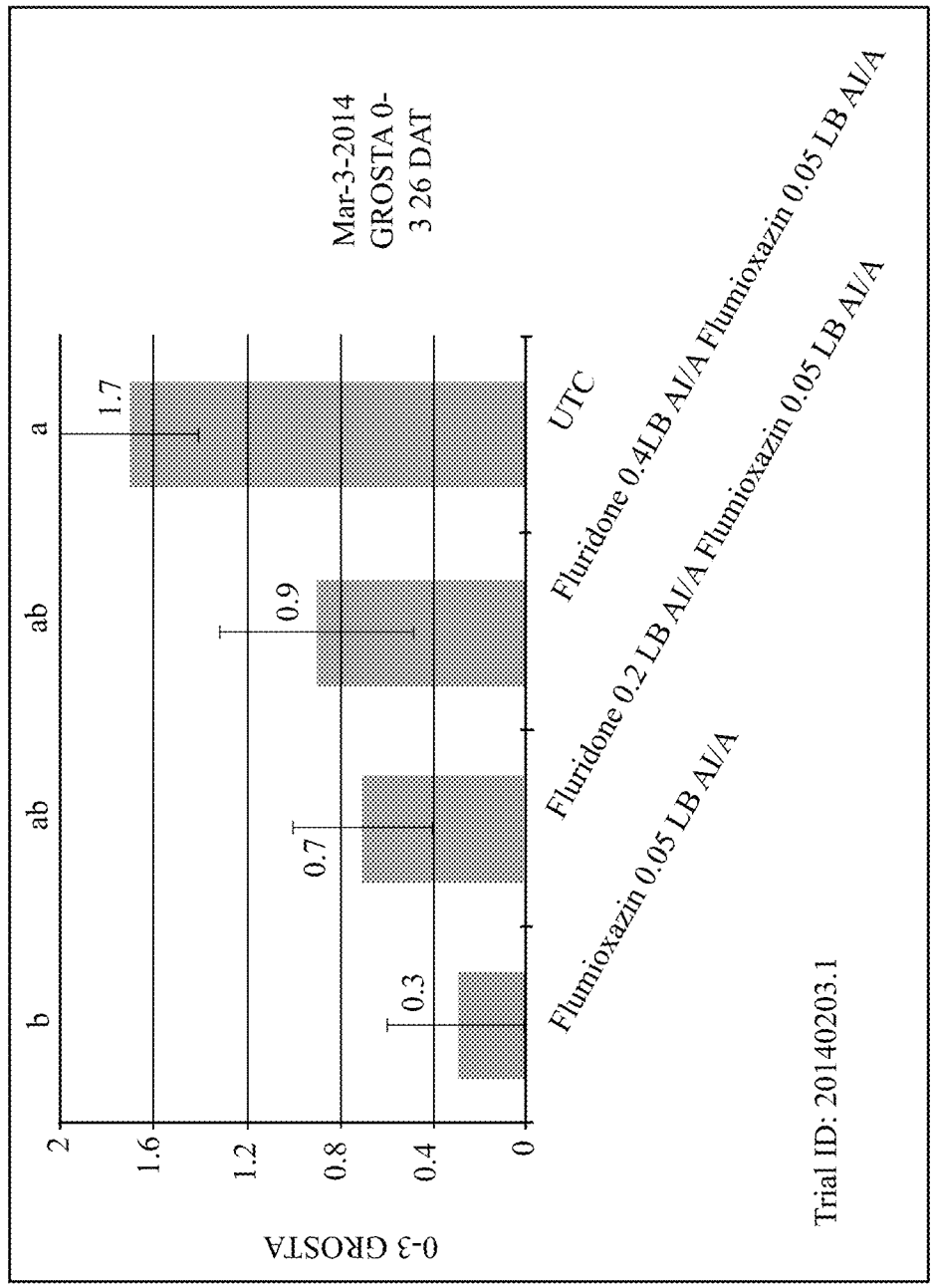
FIG. 20 shows the growth stage of cotton plants 26 days after treatment.

FIG. 20 shows the growth stage of cotton plants 26 days after treatment.

Growth stage is measured using the following scale:
0=non-emerged plant
1=emerged plant with open cotyledons
2=first true leaf stage
3=second true leaf stage As can be seen in the graph, cotton plants treated with flumioxazin at the rate of 0.05 lb/A experience the most growth stunting as compared to the untreated control plants. Growth stunting decreases as the rate of fluridone increases when used in combination with flumioxazin.

When evaluated, these data evidence that the chlorosis caused by fluridone decreased as the rate of flumioxazin increased in soybeans. It was also observed that fomesafen did not decrease the chlorosis caused by fluridone in soybean plants. In cotton, the phytotoxicity and growth inhibition caused by fomesafen was improved by the addition of fluridone to fomesafen. In cotton, the use of flumioxazin in combination with fluridone decreased crop injury as compared to when flumioxazin is used by itself.

EXAMPLE 4

Pre-emergent Application of Combinations of Fluridone with Flumioxazin or Fomesafe in Cotton and Soybeans The trial of EXAMPLE 3 was repeated using 21 replicated samples for each herbicidal application instead of 7 for each herbicidal application.

Table 6 shows the herbicide compositions applied to soybean plants of EXAMPLE 4.

TABLE 6

Herbicide compositions applied to pre-emergent soybean plants.
EXAMPLE 4: Soybean
Pre-emergent Applications of fluridone, fomesafen, and flumioxazin
on Soybean to Evaluate Injury Under Cool and Moist Conditions
Trial ID: 20140304 Protocol ID: 20140304.2

| Trt No. | Type | Treatment Name | Form Conc | Form Unit | Form Type | Rate | Rate Unit | Appl Code | Appl Description |
|---|---|---|---|---|---|---|---|---|---|
| 1 | CHK | UTC | | | | | | A | Pre-Emergent |
| 2 | HERB | Fluridone | 2 | LBA/GAL | EC | 0.075 | LBAI/A | A | Pre-Emergent |
| 3 | HERB | Fluridone | 2 | LBA/GAL | EC | 0.1 | LBAI/A | A | Pre-Emergent |
| 4 | HERB | Fluridone | 2 | LBA/GAL | EC | 0.15 | LBAI/A | A | Pre-Emergent |
| 5 | HERB | Flumioxazin | 51 | % | WG | 0.05 | LBAI/A | A | Pre-Emergent |
| 6 | HERB | Flumioxazin | 51 | % | WG | 0.1 | LBAI/A | A | Pre-Emergent |
| 7 | HERB | Flumioxazin | 51 | % | WG | 0.15 | LBAI/A | A | Pre-Emergent |
| 8 | HERB | Fluridone | 2 | LBA/GAL | EC | 0.075 | LBAI/A | A | Pre-Emergent |
|  | HERB | Flumioxazin | 51 | % | WG | 0.05 | LBAI/A | A | Pre-Emergent |
| 9 | HERB | Fluridone | 2 | LBA/GAL | EC | 0.075 | LBAI/A | A | Pre-Emergent |
|  | HERB | Flumioxazin | 51 | % | WG | 0.1 | LBAI/A | A | Pre-Emergent |
| 10 | HERB | Fluridone | 2 | LBA/GAL | EC | 0.075 | LBAI/A | A | Pre-Emergent |
|  | HERB | Flumioxazin | 51 | % | WG | 0.15 | LBAI/A | A | Pre-Emergent |
| 11 | HERB | Fluridone | 2 | LBA/GAL | EC | 0.1 | LBAI/A | A | Pre-Emergent |
|  | HERB | Flumioxazin | 51 | % | WG | 0.05 | LBAI/A | A | Pre-Emergent |
| 12 | HERB | Fluridone | 2 | LBA/GAL | EC | 0.1 | LBAI/A | A | Pre-Emergent |
|  | HERB | Flumioxazin | 51 | % | WG | 0.1 | LBAI/A | A | Pre-Emergent |
| 13 | HERB | Fluridone | 2 | LBA/GAL | EC | 0.1 | LBAI/A | A | Pre-Emergent |
|  | HERB | Flumioxazin | 51 | % | WG | 0.15 | LBAI/A | A | Pre-Emergent |
| 14 | HERB | Fluridone | 2 | LBA/GAL | EC | 0.15 | LBAI/A | A | Pre-Emergent |
|  | HERB | Flumioxazin | 51 | % | WG | 0.05 | LBAI/A | A | Pre-Emergent |
| 15 | HERB | Fluridone | 2 | LBA/GAL | EC | 0.15 | LBAI/A | A | Pre-Emergent |
|  | HERB | Flumioxazin | 51 | % | WG | 0.1 | LBAI/A | A | Pre-Emergent |
| 16 | HERB | Fluridone | 2 | LBA/GAL | EC | 0.15 | LBAI/A | A | Pre-Emergent |
|  | HERB | Flumioxazin | 51 | % | WG | 0.15 | LBAI/A | A | Pre-Emergent |
| 17 | HERB | Fomesafen | 2 | LBA/GAL | EC | 0.5 | LBAI/A | A | Pre-Emergent |
| 18 | HERB | Fomesafen | 2 | LBA/GAL | EC | 1 | LBAI/A | A | Pre-Emergent |
| 19 | HERB | Fluridone | 2 | LBA/GAL | EC | 0.1 | LBAI/A | A | Pre-Emergent |
|  | HERB | Fomesafen | 2 | LBA/GAL | EC | 0.5 | LBAI/A | A | Pre-Emergent |
| 20 | HERB | Fluridone | 2 | LBA/GAL | EC | 0.1 | LBAI/A | A | Pre-Emergent |
|  | HERB | Fomesafen | 2 | LBA/GAL | EC | 1 | LBAI/A | A | Pre-Emergent |

Table 7 shows the herbicide compositions applied to cotton plants of EXAMPLE 4.

TABLE 7

Herbicide compositions applied to pre-emergent cotton plants.
EXAMPLE 4: Cotton
Pre-emergent Applications of fluridone, fomesafen, and flumioxazin
on Cotton to Evaluate Injury Under Cool and Moist Conditions

| Trt No. | Type | Treatment Name | Form Conc | Form Unit | Form Type | Rate | Rate Unit | Appl Code | Appl Description |
|---|---|---|---|---|---|---|---|---|---|
| 1 | CHK | UTC | | | | | | A | Pre-Emergent |
| 2 | HERB | Fluridone | 2 | LBA/GAL | EC | 0.1 | LBAI/A | A | Pre-Emergent |
| 3 | HERB | Fluridone | 2 | LBA/GAL | EC | 0.2 | LBAI/A | A | Pre-Emergent |
| 4 | HERB | Flumioxazin | 51 | % | WG | 0.025 | LBAI/A | A | Pre-Emergent |
| 5 | HERB | Flumioxazin | 51 | % | WG | 0.033 | LBAI/A | A | Pre-Emergent |
| 6 | HERB | Flumioxazin | 51 | % | WG | 0.05 | LBAI/A | A | Pre-Emergent |
| 7 | HERB | Fluridone | 2 | LBA/GAL | EC | 0.1 | LBAI/A | A | Pre-Emergent |
|   | HERB | Flumioxazin | 51 | % | WG | 0.025 | LBAI/A | A | Pre-Emergent |
| 8 | HERB | Fluridone | 2 | LBA/GAL | EC | 0.1 | LBAI/A | A | Pre-Emergent |
|   | HERB | Flumioxazin | 51 | % | WG | 0.033 | LBAI/A | A | Pre-Emergent |
| 9 | HERB | Fluridone | 2 | LBA/GAL | EC | 0.1 | LBAI/A | A | Pre-Emergent |
|   | HERB | Flumioxazin | 51 | % | WG | 0.05 | LBAI/A | A | Pre-Emergent |
| 10 | HERB | Fluridone | 2 | LBA/GAL | EC | 0.2 | LBAI/A | A | Pre-Emergent |
|   | HERB | Flumioxazin | 51 | % | WG | 0.025 | LBAI/A | A | Pre-Emergent |
| 11 | HERB | Fluridone | 2 | LBA/GAL | EC | 0.2 | LBAI/A | A | Pre-Emergent |
|   | HERB | Flumioxazin | 51 | % | WG | 0.033 | LBAI/A | A | Pre-Emergent |
| 12 | HERB | Fluridone | 2 | LBA/GAL | EC | 0.2 | LBAI/A | A | Pre-Emergent |
|   | HERB | Flumioxazin | 51 | % | WG | 0.05 | LBAI/A | A | Pre-Emergent |
| 13 | HERB | Fomesafen | 2 | LBA/GAL | EC | 0.125 | LBAI/A | A | Pre-Emergent |
| 14 | HERB | Fomesafen | 2 | LBA/GAL | EC | 0.25 | LBAI/A | A | Pre-Emergent |
| 15 | HERB | Fomesafen | 2 | LBA/GAL | EC | 0.375 | LBAI/A | A | Pre-Emergent |
| 16 | HERB | Fluridone | 2 | LBA/GAL | EC | 0.1 | LBAI/A | A | Pre-Emergent |
|   | HERB | Fomesafen | 2 | LBA/GAL | EC | 0.125 | LBAI/A | A | Pre-Emergent |
| 17 | HERB | Fluridone | 2 | LBA/GAL | EC | 0.1 | LBAI/A | A | Pre-Emergent |
|   | HERB | Fomesafen | 2 | LBA/GAL | EC | 0.25 | LBAI/A | A | Pre-Emergent |
| 18 | HERB | Fluridone | 2 | LBA/GAL | EC | 0.1 | LBAI/A | A | Pre-Emergent |
|   | HERB | Fomesafen | 2 | LBA/GAL | EC | 0.375 | LBAI/A | A | Pre-Emergent |
| 19 | HERB | Fluridone | 2 | LBA/GAL | EC | 0.2 | LBAI/A | A | Pre-Emergent |
|   | HERB | Fomesafen | 2 | LBA/GAL | EC | 0.125 | LBAI/A | A | Pre-Emergent |
| 20 | HERB | Fluridone | 2 | LBA/GAL | EC | 0.2 | LBAI/A | A | Pre-Emergent |
|   | HERB | Fomesafen | 2 | LBA/GAL | EC | 0.25 | LBAI/A | A | Pre-Emergent |
| 21 | HERB | Fluridone | 2 | LBA/GAL | EC | 0.2 | LBAI/A | A | Pre-Emergent |
|   | HERB | Fomesafen | 2 | LBA/GAL | EC | 0.375 | LBAI/A | A | Pre-Emergent |

Figure 24:
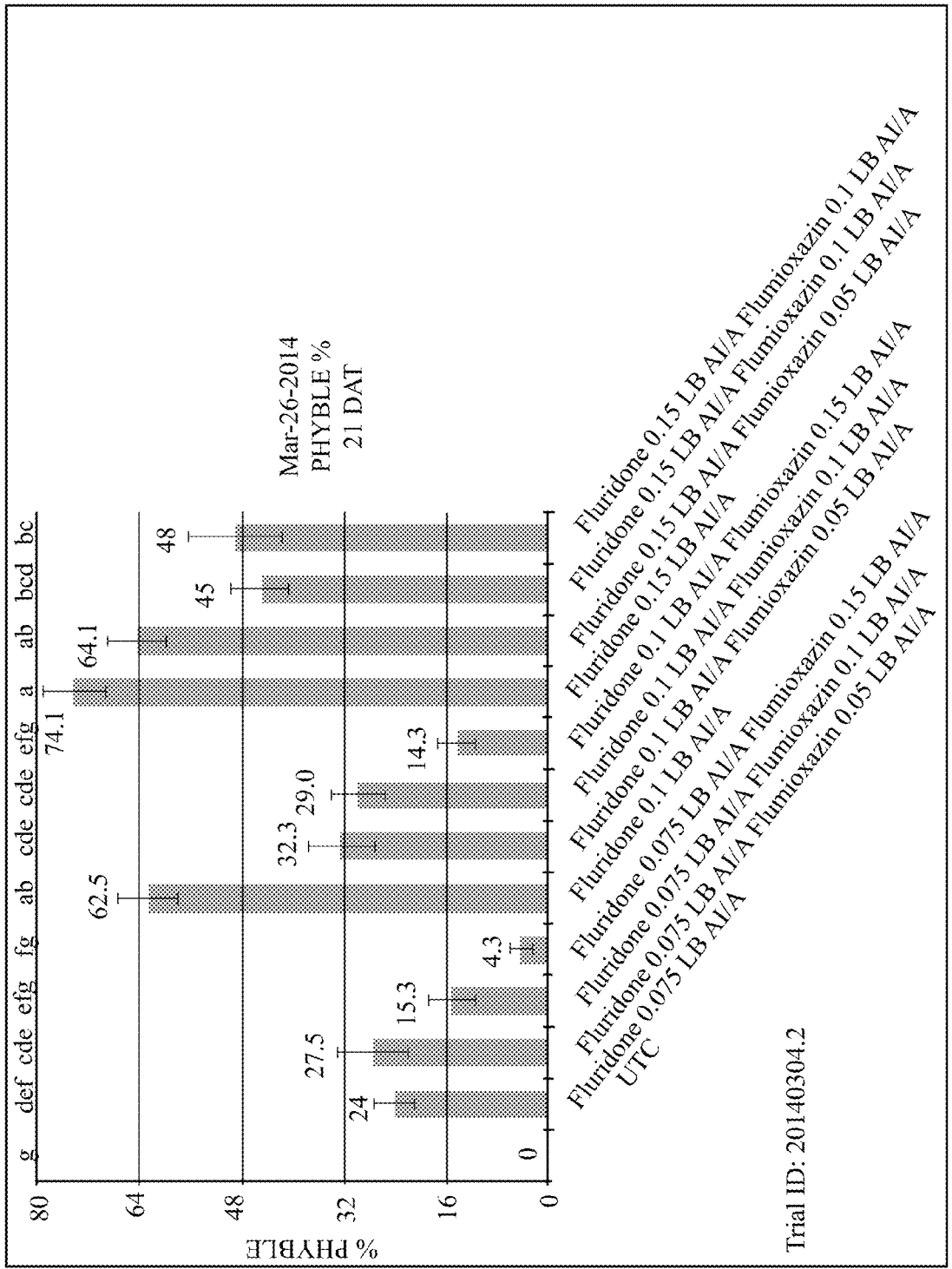
FIG. 24 shows the percent chlorosis observed 21 days after treatment of soybean plants with herbicidal compositions.

Soybeans:

FIG. 24 shows the percent chlorosis observed 21 days after treatment of soybean plants with various herbicidal compositions. A decrease in chlorosis is observed as the rate of flumioxazin is increased when used with fluridone.

Figure 25:
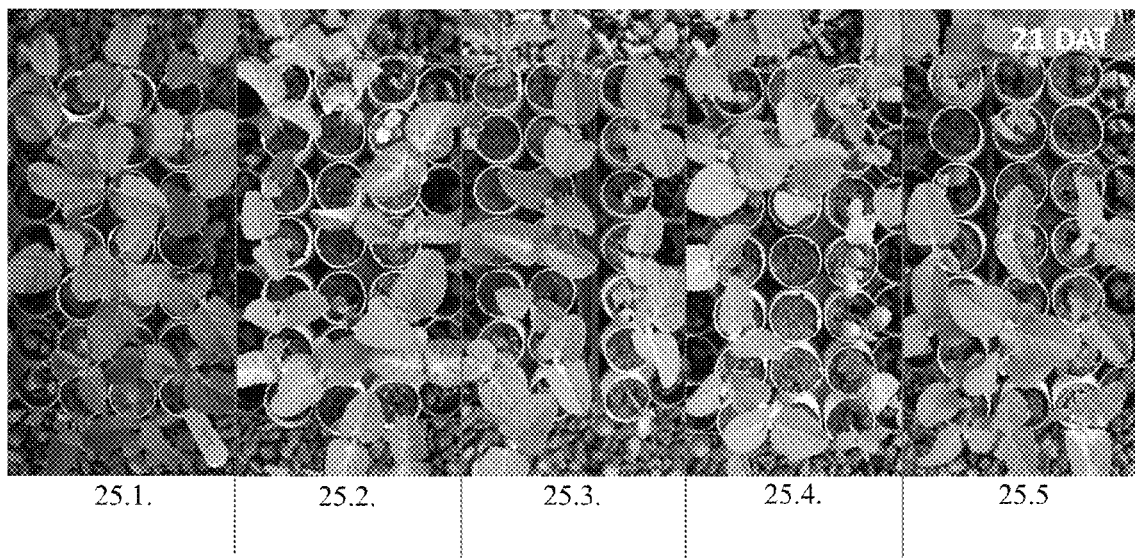
FIG. 25 shows a series of digital images of soybean plants treated with herbidical compositions. 25.1. is untreated control (UTC). 25.2. is Fluridone 0.1 lb /ai/A. 25.3. is Fluridone 0.1 lb ai/A+Flumioxazin 0.05 lb ai/A. 25.4. is Fluridone 0.1 lb ai/A+Flumioxazin 0.1 lb ai/A. 25.5. is Fluridone 0.1 lb ai/A+Flumioxazin 0.15 lb ai/A.

FIG. 25 shows a series of digital images of soybean plants treated with various herbicide compositions including 0.1 lb/A fluridone; 0.1 lb/A fluridone and 0.05 lb/A flumioxazin; 0.1 lb/A fluridone and 0.1 lb/A flumioxazin; and 0.1 lb/A fluridone and 0.15 lb/A flumioxazin.

These data evidence that in soybean plants, flumioxazin safens fluridone by decreasing the chlorosis observed.

Figure 21:
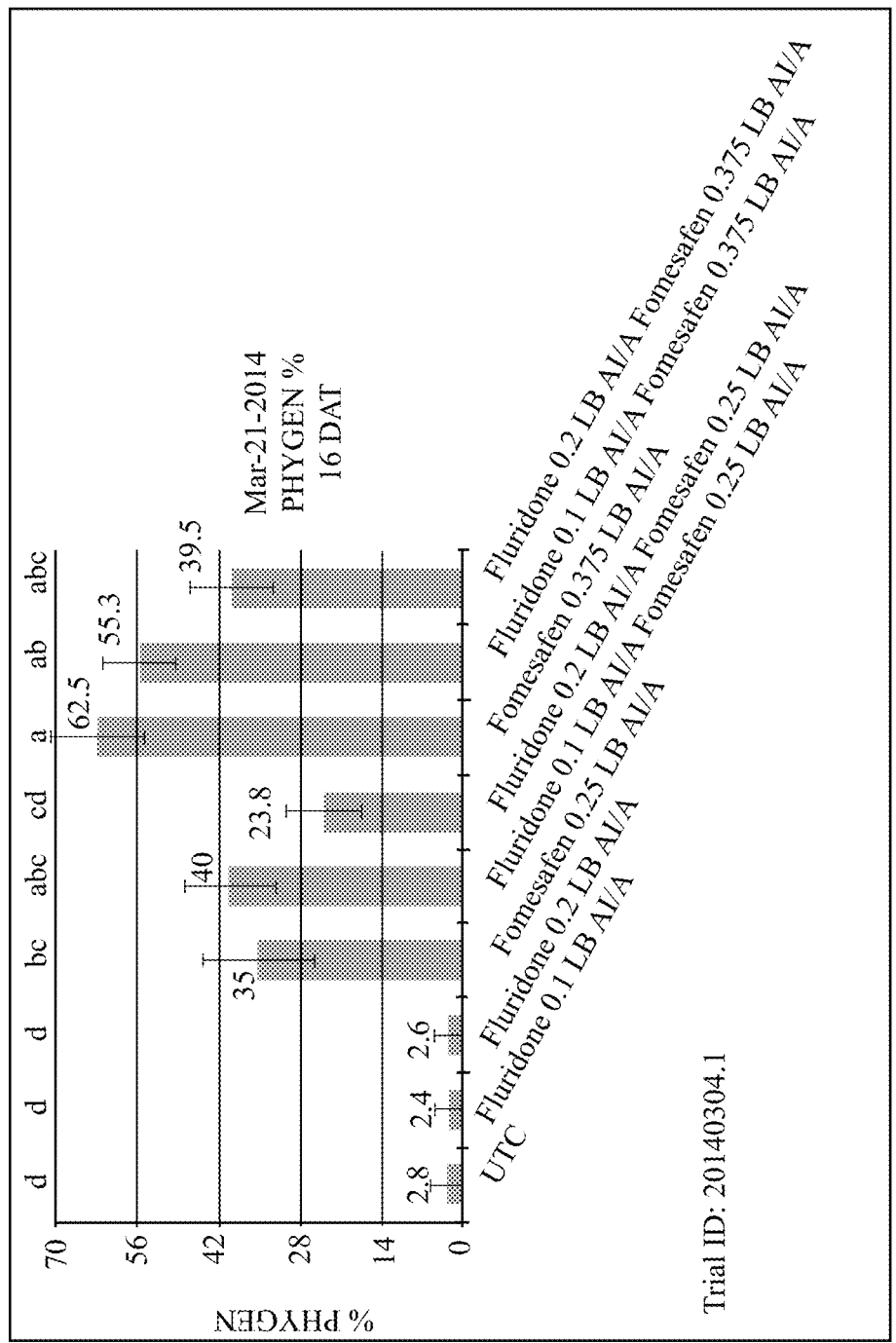
FIG. 21 shows the damage to cotton plants 16 days after treatment with herbicidal compositions.
Figure 22:
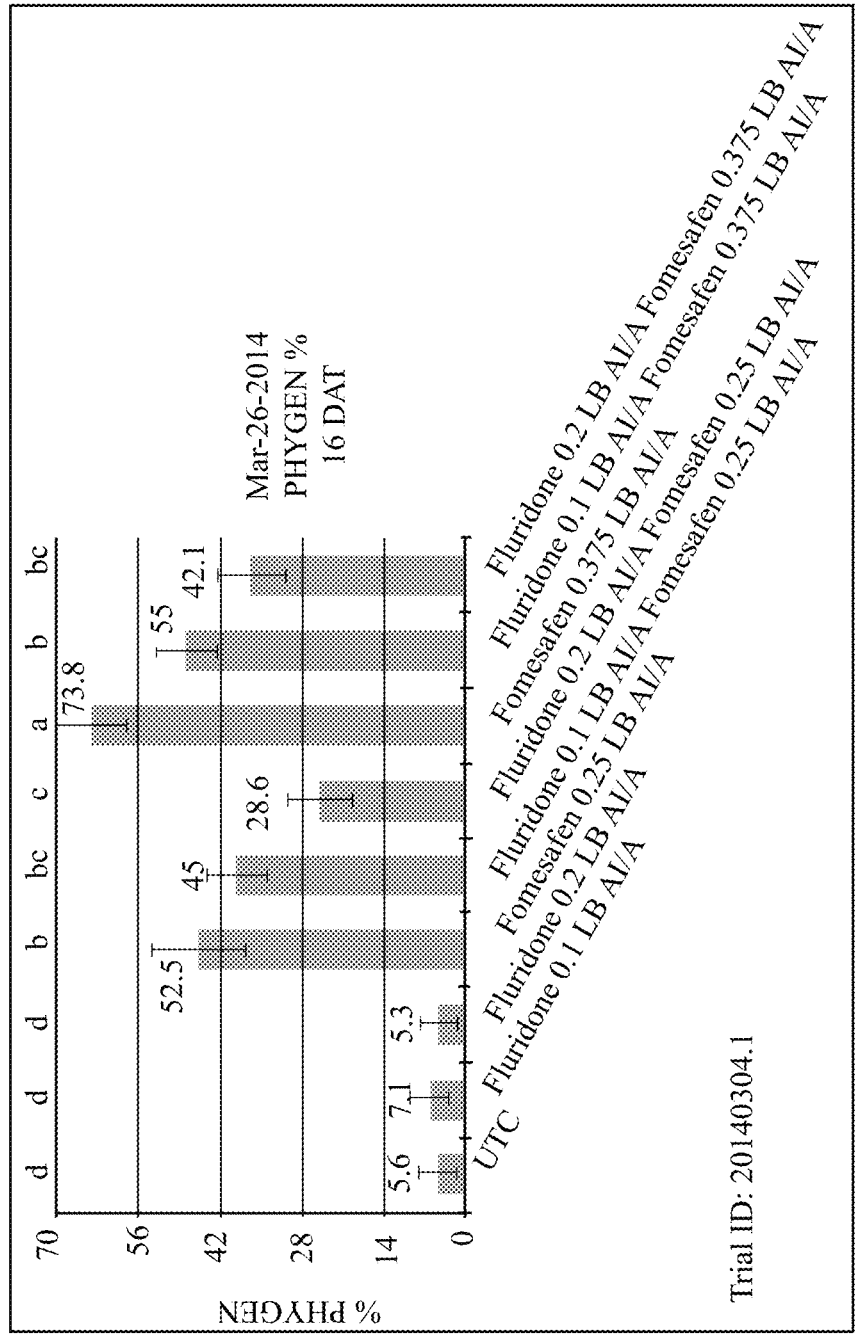
FIG. 22 shows the damage to cotton plants 21 days after treatment with herbicidal compositions.

Cotton:

FIG. 21 and FIG. 22 show the damage to cotton plants 16 days after treatment and 21 days after treatment with various herbicidal compositions as measured by the percentage of cotyledons with excessive wrinkling and brown spotting due to herbicide injury. These data evidence that fluridone is safening fomesafen as the damage observed decreases when the application rate of fomesafen is increased when used in conjunction with fluridone.

Figure 23:
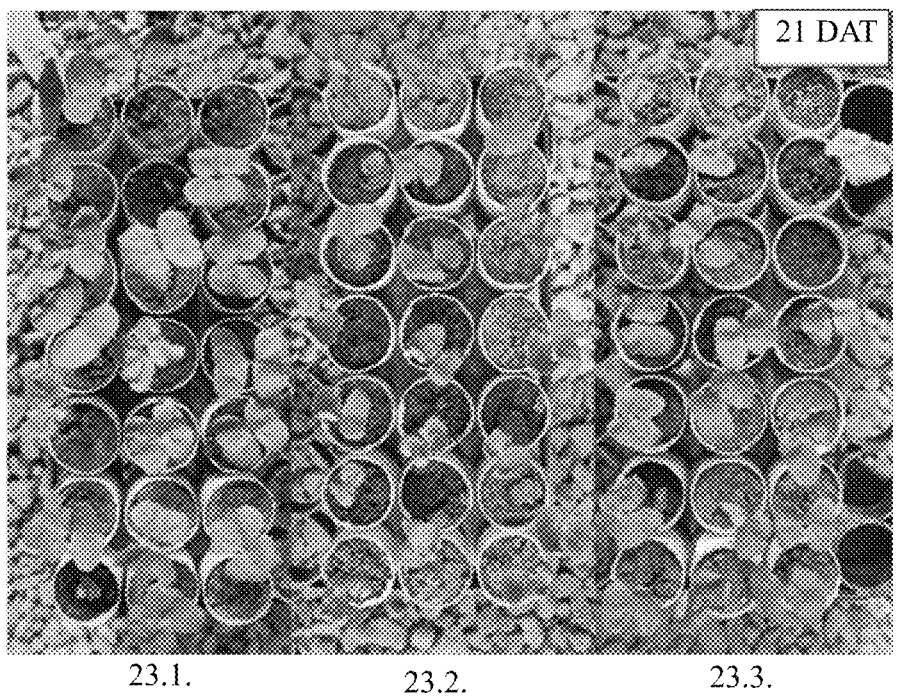
FIG. 23 shows three digital images of cotton plants treated with herbicidal compositions. 21.1. is untreated control (UTC). 23.2. is fomesafen 0.375 lb ai/A. 23.3 is Fomesafen+Fluridone 0.375:0.2 lb ai/A.

FIG. 23 shows a series of three digital images of cotton plants treated with fomesafen alone, fomesafen applied with fluridone, and an untreated control group.

These data evidence that in cotton plants, fluridone safens fomesafen by reducing the injury to plants observed as the number of cotyledons with excessive wrinkling or brown spotting and that fluridone safens flumioxazin by reducing the injury to plants observed as the number of cotyledons with excessive wrinkling or brown spotting.

EXAMPLE 5

Pre-emergent Application of Combinations of Fluridone with Flumioxazin in Corn

Materials and Methods:

A greenhouse trial was conducted to determine if fluridone and flumioxazin have a safening effect on the other when applied to corn plants prior to emergence from the soil. Ten compositions were applied to corn plants after corn seed had been planted, but prior to the corn plants emergence from the soil, and each application was repeated seven times. The herbicidal compositions applied are described in Table 8, where there is an untreated control (Application No. 1), fluridone applied alone (Applications Nos. 5-7), flumioxazin applied alone (Application Nos. 2-4), and combinations of fluridone and flumioxazin (Application Nos. 8-10).

TABLE 8

Applications of herbicidal compositions to corn plants applied pre-emersent to the plants.

| Application No. | Rate Fluridone Applied | Rate Flumioxazin Applied | Units |
|---|---|---|---|
| 1 | 0 | 0 | lb/A |
| 2 | 0 | 0.05 | lb/A |
| 3 | 0 | 0.1 | lb/A |
| 4 | 0 | 0.15 | lb/A |
| 5 | 0.05 | 0 | lb/A |
| 6 | 0.1 | 0 | lb/A |
| 7 | 0.15 | 0 | lb/A |
| 8 | 0.05 | 0.05 | lb/A |
| 9 | 0.1 | 0.1 | lb/A |
| 10 | 0.15 | 0.15 | lb/A |

Figure 26:
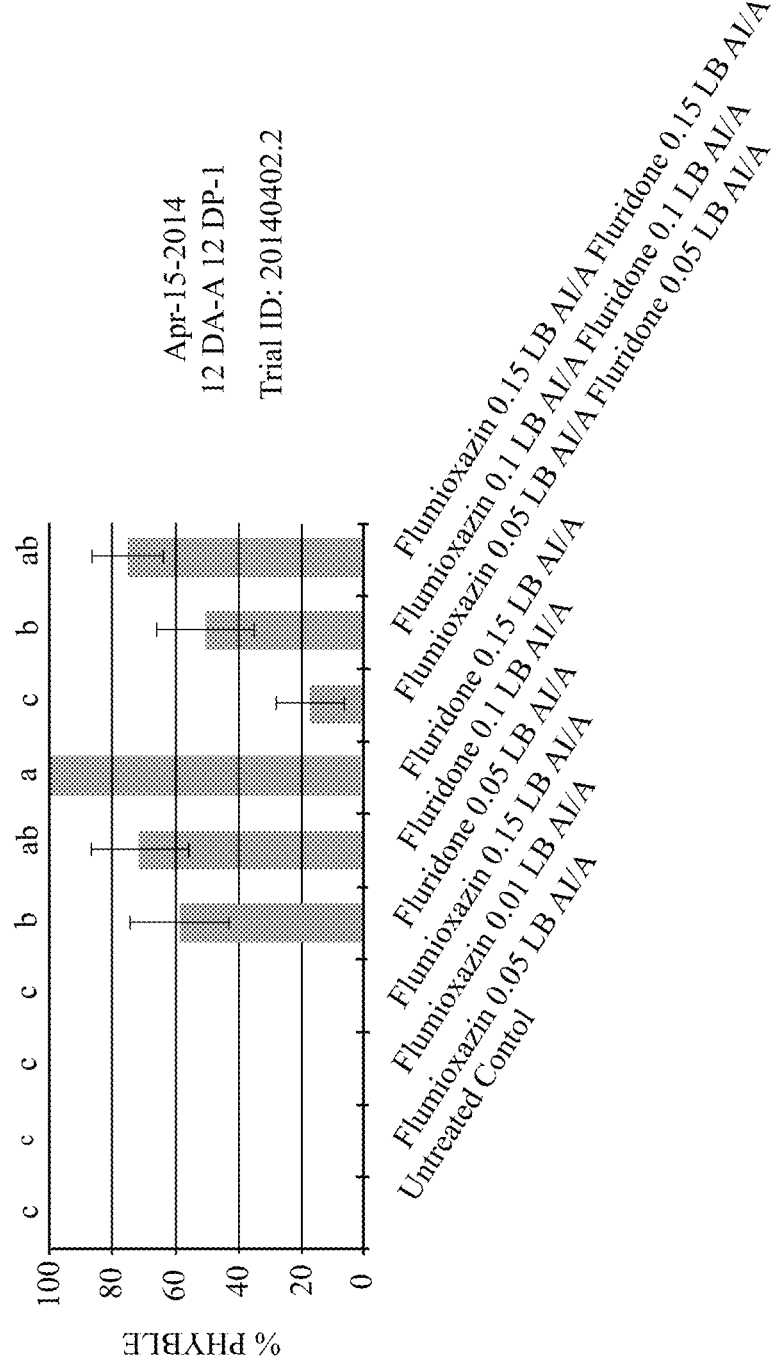
FIG. 26 shows the percentage of leaves with visible bleaching injury (% PHYBLE) when various herbicidal compositions are applied to corn plants.

Results:

FIG. 26 shows the percentage of leaves with visible bleaching injury measured 12 days after application (% PHYBLE) when various herbicidal compositions are applied to corn plants. As can be seen from this bar graph, the percentage of leaves with visible bleaching damage, a measure of chlorosis, decreases when a combination of fluridone and flumioxazin is used as compared to when fluridone is used alone. These data evidence that flumioxazin is safening fluridone on cotton plants as measured by the percentage of leaves with visible bleaching injury.

Figure 27:
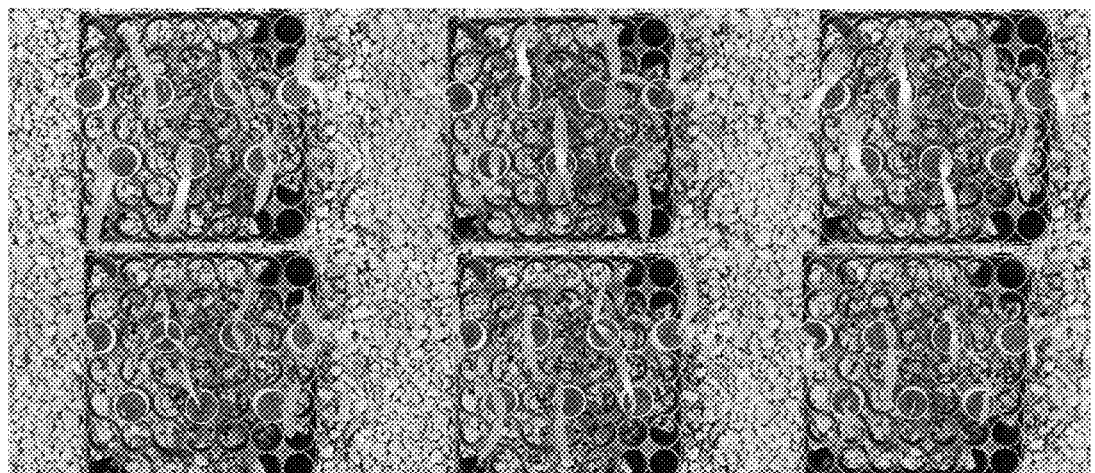
FIG. 27 shows a digital image of corn plants when various herbicidal compositions are applied. 27.1. is Fluridone 0.05 lb ai/A. 27.2. is Fluridone 0.1 lb ai/A. 27.3. is Fluridone 0.15 lb ai/A. 27.4. is Fluridone 0.05 lb ai/A+Flumioxazin 0.05 lb ai/A. 27.5. is Fluridone 0.1 lb ai/A+Flumioxazin 0.1 lb ai/A. 27.6. is Fluridone 0.15 lb ai/A+Flumioxazin 0.15 lb ai/A.

FIG. 27 shows a digital image of corn plants when various herbicidal compositions are applied. The image was taken 12 days after treatment.

Figure 28:
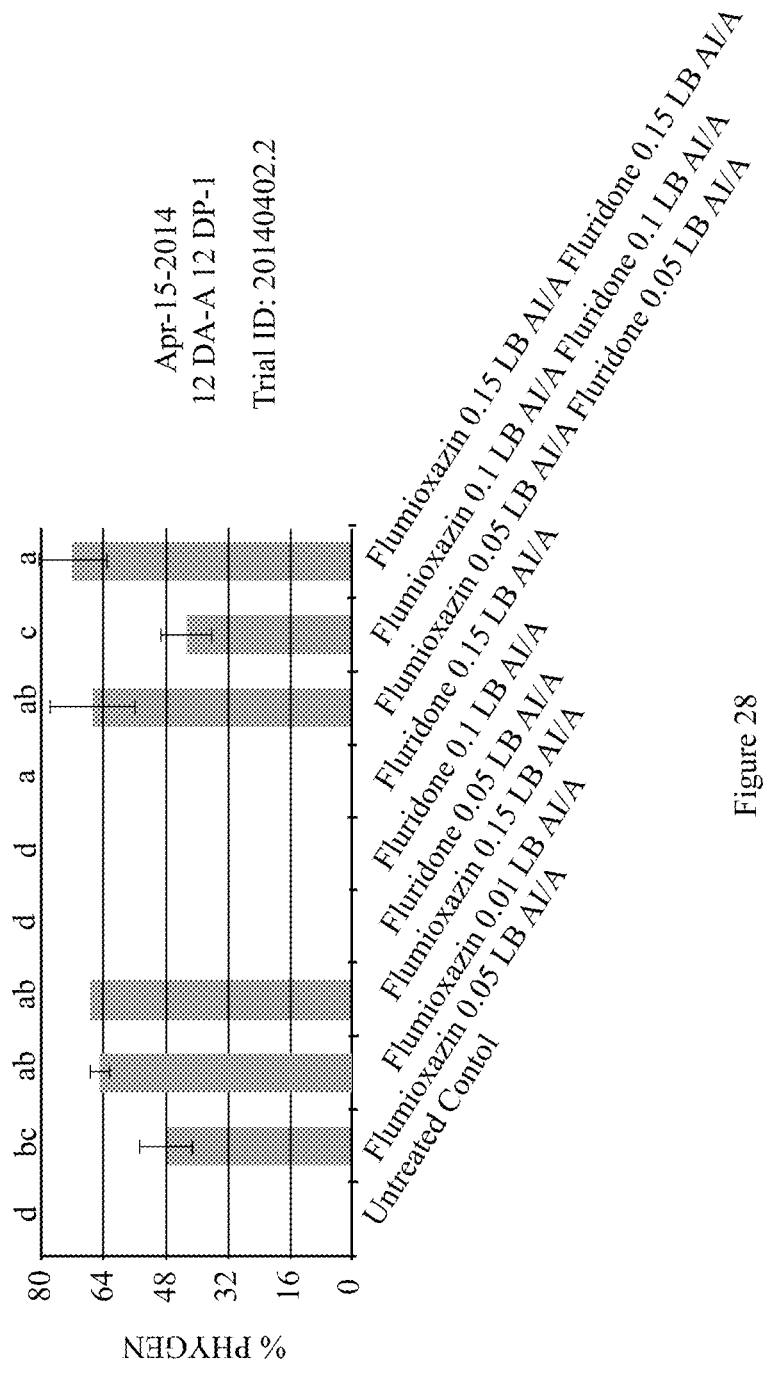
FIG. 28 shows the percentage of cotyledons with excessive wrinkling and brown spotting due to herbicide injury observed on cotton plants when various herbicidal compositions are applied.

FIG. 28 shows the percentage of cotyledons with excessive wrinkling and brown spotting due to herbicide injury observed on cotton plants when various herbicidal compositions are applied (% PHYGEN) measured 12 days after application. These data show, in particular, that when fluridone is applied at a rate of 0.1 lb/A and flumioxazin is applied at the rate of 0.1 lb/A the percentage of cotyledons with excessive wrinkling and brown spotting due to herbicide injury is decreased as compared to when flumioxazin is applied alone.

Figure 29:
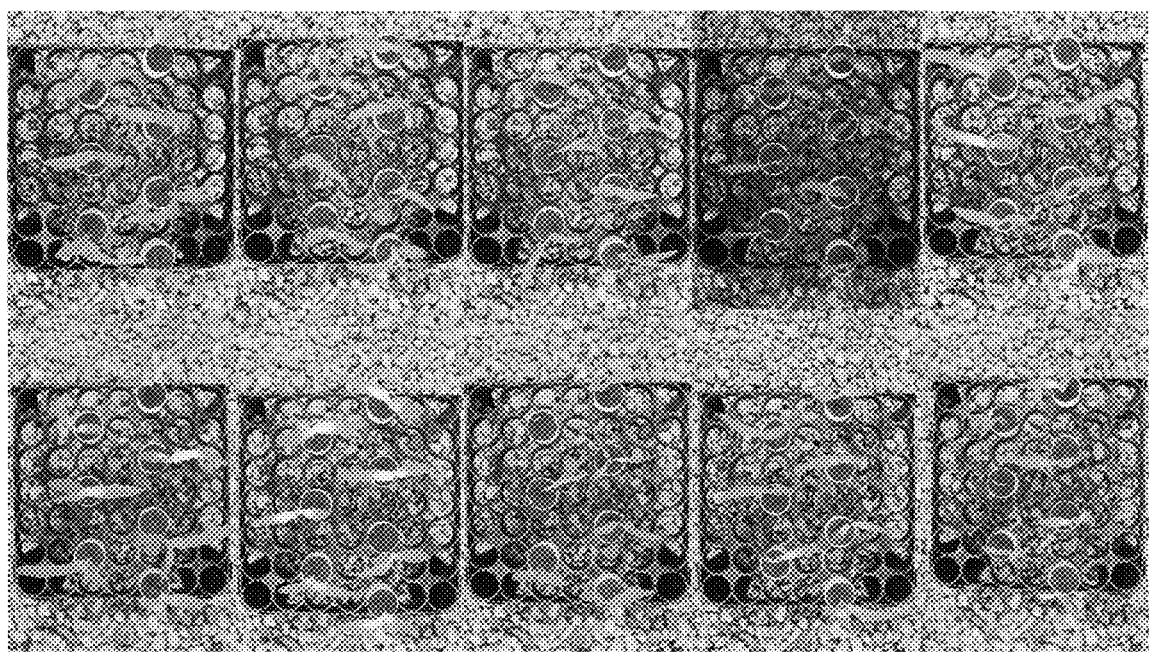
FIG. 29 shows digital images of corn plants when various herbicidal compositions are applied.

FIG. 29 shows digital images of corn plants when various herbicidal compositions are applied. The image was captured 12 days after treatment.

The uses of the terms "a" and "an" and "the" and similar references in the context of describing the invention (especially in the context of the following claims) are to be construed to cover both the singular and the plural unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention. While the invention has been illustrated and described in detail in the drawings and the foregoing description, the same is to be considered as illustrative and not restrictive in character, it being understood that only the preferred embodiment has been shown and described and that all changes and modifications that come within the spirit of the invention are desired to be protected. In addition, all references cited herein are indicative of the level of skill in the art and are hereby incorporated by reference in their entirety.

What is claimed is:

1. A method for controlling weeds while generating crop plants, comprising the steps of:
    planting plant-generating material in soil for generating crop plants;
    applying fluridone to the soil before the crop plants emerge from the soil;
    applying fomesafen or flumioxazin to the soil before the crop plants emerge from the soil; and
    wherein (i) said applying fluridone safens the crop from exposure to the fomesafen or flumioxazin or (ii) said applying fomesafen or flumioxazin safens the crop from exposure to the fluridone.

2. The method of claim 1, wherein the crop plants are cotton plants, wherein said applying fluriode safens the crop from exposure to the fomesafen or flumioxazin.

3. The method of claim 2, wherein said applying fomesafen or flumioxazin comprises applying fomesafen.

4. The method of claim 3, wherein the crop-generating material is cotton seeds.

5. The method of claim 4, wherein the weeds are *Amaranthus* weeds.

6. The method of claim 5, wherein the cotton plants are glyphosate resistant cotton plants.

7. The method of claim 2, wherein said applying fomesafen or flumioxazin comprises applying flumioxazin.

8. The method of claim 7, wherein the cotton plants are glyphosate resistant cotton plants.

9. The method of claim 1, wherein the crop plants are soybean plants, wherein said applying fomesafen or flumioxazin safens the crop from exposure to the fluridone.

10. The method of claim 9, wherein said applying fomesafen or flumioxazin comprises applying fomesafen.

11. The method of claim 10, wherein the crop-generating material is soybean seeds.

12. The method of claim 11, wherein said soybean plants are glyphosate resistant soybean plants.

13. The method of claim 9, wherein said applying fomesafen or flumioxazin comprises applying flumioxazin.

14. The method of claim 13, wherein the crop-generating material is soybean seeds.

15. The method of claim 14, wherein said soybean plants are glyphosate resistant soybean plants.

16. The method of claim 1, wherein said applying fluridone is conducted in advance of said planting plant-generating material.

17. A method of claim 1, wherein: for weed control for cotton plants, comprising:
    said crop plants are cotton plants; and
    said step of planting plant-generating material in soil for generating crop plants comprises planting cotton seeds in the soil.

18. The method of claim 17, also comprising safening the fomesafen or flumioxazin with the fluridone.

19. The method of claim 1 wherein:
    said crop plants are soybean plants; and
    said step of planting plant-generating material in soil for generating crop plants comprises planting soybean seeds in the soil.

20. The method of claim 19, wherein said applying fomesafen or flumioxazin safens the crop from exposure to the fluridone.

21. A method for controlling weeds while generating cotton plants, comprises the steps of:
- planting cotton seeds in soil for generating cotton plants;
- applying fluriode to the soil before the cotton plants emerge from the soil;
- applying fomesafen or flumioxazin to the soil before the cotton plants emerge from the soil; and
- wherein said applying fluridone safens the cotton plants from exposure to the fomesafen of flumioxazin;
- wherein said applying fluridone to the soil comprises applying from about 0.1 to about 0.4 pounds fluriodne per acre to the soil; and
- wherein said applying fomesafen or flumioxazin comprises applying about 0.05 to about 0.4 pounds fomesafen per acre to the soil or or from about 0.025 to about 0.25 pounds flumioxazin per acre to the soil.

22. The method of claim 21, said applying fluridone reduces the percent chlorosis in the cotton plants relative to the method without applying fluridone.

23. The method of claim 21, said applying fluridone increases the height of the cotton plants relative to the method without applying fluridone.

24. The method of claim 21, said applying fluridone increases the crop stand of the cotton plants relative to the method without applying fluridone.

25. The method of claim 21, said applying fluridone reduces the number of brown spots on plant leaves of the cotton plants relative to the method without applying fluridone.

26. A method for controlling weeds while generating cotton plants, comprising the steps of:
- planting cotton seeds in soil for generating cotton plants;
- applying fluridone to the soil before the cotton plants emerge from the soil;
- applying fomesafen or flumioxazin to the soil before the cotton plants emerge from the soil; and
- wherein said applying fluridone reduces a phytotoxic response of the cotton plants relative to the method without applying fluridone.

27. The method of claim 26, wherein the reduced phytotoxic response is evidenced by at least one selected from the group consisting of a reduced percent chlorosis of the cotton plants, increased plant height of the cotton plants, improved crop stand of the cotton plants, and a reduced number of brown spots on leaves of the cotton plants.

28. The method of claim 26, wherein said applying fluridone to the soil comprises applying from about 0.1 to about 0.4 pounds fluridone per acre to the soil.

29. The method of claim 26, wherein said applying fomesafen or flumioxazin comprises applying about 0.05 to about 0.4 pounds fomesafen per acre to the soil or or from about 0.025 to about 0.25 pounds flumioxazin per acre to the soil.

30. The method of claim 26, wherein said applying fluridone to the soil comprises applying from about 0.1 to about 0.4 pounds fluridone per acre to the soil; and wherein said applying fomesafen or flumioxazin comprises applying about 0.05 to about 0.4 pounds fomesafen per acre to the soil or or from about 0.025 to about 0.25 pounds flumioxazin per acre to the soil.

\* \* \* \* \*